(12) United States Patent
Neff et al.

(10) Patent No.: US 10,165,773 B2
(45) Date of Patent: Jan. 1, 2019

(54) ANTIMICROBIAL CONSTRUCTS

(71) Applicants: Jennifer A. Neff, Rancho Santa Margarita, CA (US); Joseph McGuire, Corvallis, OR (US); Pranav Joshi, Bangalore (IN)

(72) Inventors: Jennifer A. Neff, Rancho Santa Margarita, CA (US); Joseph McGuire, Corvallis, OR (US); Pranav R. Joshi, Bangalore (IN)

(73) Assignees: Allvivio Vascular, Inc., Lake Forest, CA (US); State of Oregon acting by and through the State Board of Higher Ed. on Behalf of Oregon State Univ., Corvallis, OR (US)

( * ) Notice: Subject to any disclaimer, the term of this patent is extended or adjusted under 35 U.S.C. 154(b) by 0 days.

(21) Appl. No.: 14/464,589

(22) Filed: Aug. 20, 2014

(65) Prior Publication Data

US 2014/0356405 A1 Dec. 4, 2014

Related U.S. Application Data

(63) Continuation of application No. 14/094,577, filed on Dec. 2, 2013, now abandoned, which is a continuation
(Continued)

(51) Int. Cl.
*C08L 71/02* (2006.01)
*A01N 25/10* (2006.01)
(Continued)

(52) U.S. Cl.
CPC .............. *A01N 25/10* (2013.01); *A01N 25/34* (2013.01); *A01N 63/02* (2013.01); *A23L 3/3463* (2013.01);
(Continued)

(58) Field of Classification Search
None
See application file for complete search history.

(56) References Cited

U.S. PATENT DOCUMENTS

| 3,826,678 A | 7/1974 | Hoffman et al. |
| 5,618,528 A | 4/1997 | Cooper et al. |

(Continued)

OTHER PUBLICATIONS

Neff et al. "A novel method for surface modification to promote cell attachment to hydrophobic substrates" J. Biomed. Mater. Res. 40, 1998, 511-519.*
(Continued)

*Primary Examiner* — Robert S Loewe
(74) *Attorney, Agent, or Firm* — Karish & Bjorgum, PC; Kristin C. Hiibner

(57) ABSTRACT

The invention is based on the recognition that known antimicrobial compounds, such as nisin or other lantibiotics, can be made to form a long lasting antimicrobial surface coating by linking the peptide with a block polymer, such as PLURONIC® F108 or an end group activated polymer (EGAP) in a manner to form a flexible tether and/or entrap the peptide. The entrapped peptide provides antimicrobial action by early release from entrapment while the tethered peptide provides longer lasting antimicrobial protection. Antimicrobial gels and foams may be prepared using the antimicrobial peptide containing block copolymers.

30 Claims, 23 Drawing Sheets

Related U.S. Application Data of application No. 13/472,346, filed on May 15, 2012, now Pat. No. 8,598,269, which is a continuation of application No. 12/171,593, filed on Jul. 11, 2008, now Pat. No. 8,178,617.

(60) Provisional application No. 60/950,080, filed on Jul. 16, 2007.

(51) Int. Cl.

| | | |
|---|---|---|
| *A01N 25/34* | (2006.01) | |
| *A23L 3/3463* | (2006.01) | |
| *A61K 47/48* | (2006.01) | |
| *C08G 65/334* | (2006.01) | |
| *C08K 9/08* | (2006.01) | |
| *A01N 63/02* | (2006.01) | |
| *A61L 2/232* | (2006.01) | |

(52) U.S. Cl.
CPC .. *A61K 47/48215* (2013.01); *A61K 47/48992* (2013.01); *C08G 65/3348* (2013.01); *C08K 9/08* (2013.01); *C08L 71/02* (2013.01); *A61L 2/232* (2013.01); *C08G 2650/58* (2013.01); *C08K 2201/013* (2013.01); *C08L 2205/05* (2013.01); *Y10T 428/1352* (2015.01); *Y10T 428/1376* (2015.01)

(56) References Cited

U.S. PATENT DOCUMENTS

| | | | |
|---|---|---|---|
| 5,763,395 A | 6/1998 | Blackburn et al. | |
| 5,783,178 A | 7/1998 | Kabanov et al. | |
| 5,945,457 A | 8/1999 | Plate et al. | |
| 6,096,728 A | 8/2000 | Collins et al. | |
| 6,106,866 A | 8/2000 | Ranney | |
| 6,113,815 A | 9/2000 | Elfersy et al. | |
| 6,143,354 A | 11/2000 | Koulik et al. | |
| 6,258,351 B1 | 7/2001 | Harris | |
| 6,383,500 B1 | 5/2002 | Wooley et al. | |
| 6,545,097 B2 | 4/2003 | Pinchuk et al. | |
| 6,596,401 B1 | 7/2003 | Terry et al. | |
| 6,730,334 B2 | 5/2004 | Zhao | |
| 6,852,776 B2 | 2/2005 | Ong et al. | |
| 6,968,234 B2 | 11/2005 | Stokes | |
| 7,029,755 B2 | 4/2006 | Terry et al. | |
| 7,053,150 B2 | 5/2006 | Kozlowski et al. | |
| 7,132,475 B2 | 11/2006 | Hubbell et al. | |
| 7,279,175 B2 | 10/2007 | Chen et al. | |
| 8,178,617 B2 | 5/2012 | Neff et al. | |
| 8,598,269 B2 | 12/2013 | Neff et al. | |
| 2002/0042473 A1 | 4/2002 | Trollsas et al. | |
| 2003/0149173 A1 | 8/2003 | Rhee et al. | |
| 2003/0215436 A1 | 11/2003 | Walsh et al. | |
| 2004/0001872 A1 | 1/2004 | Shih et al. | |
| 2004/0204548 A1 | 10/2004 | Kozlowski et al. | |
| 2004/0235137 A1 | 11/2004 | Qi et al. | |
| 2005/0101692 A1 | 5/2005 | Sohier et al. | |
| 2005/0244456 A1 | 11/2005 | Nilsson et al. | |
| 2005/0244459 A1 | 11/2005 | DeWitt et al. | |
| 2005/0281866 A1 | 12/2005 | Jarrett et al. | |
| 2006/0099567 A1 | 5/2006 | Muller-Cohn et al. | |
| 2006/0121083 A1 | 6/2006 | Mor | |
| 2006/0239960 A1 | 10/2006 | Bossard et al. | |
| 2007/0224162 A1 | 9/2007 | Roby et al. | |
| 2007/0292404 A1 | 12/2007 | Walsh et al. | |

OTHER PUBLICATIONS http://www.drugfuture.com/Pharmacopoela/USP32/pub/data/v32270/usp32nf27s0_m66210.html, 3 pages, no date given.

Grillet, Anne M. et al., "Polymer Gel Rheology and Adhesion;" www.intechopen.com; Sandia National Laboratories, USA; pp. 59-81.

International Search Report, PCT/US2008/069827, dated Jan. 29, 2009.

Blazanovic, et al., "Structure-based redesign of lysostaphin yields potent antistaphylococcal enzymes that evade immune cell surveillance", Molecular Therapy—Methods & Clinical Development (2015) 2, 15021.

Veronese, F.M., "PEGylated Protein Drugs: Basic Science and Clinical Applications", Springer Science & Business Media, Dec. 30, 2009, p. 22.

\* cited by examiner

ANTIMICROBIAL CONSTRUCTS

CROSS-REFERENCE TO RELATED APPLICATIONS

This Application is a continuation of and claims the benefit of U.S. patent application Ser. No. 14/094,577, which is a continuation of U.S. patent application Ser. No. 13/472,346, filed May 15, 2012, now U.S. Pat. No. 8,598,269, which is a continuation of U.S. patent application Ser. No. 12/171,593, filed Jul. 11, 2008, now U.S. Pat. No. 8,178,617, which claims the benefit of U.S. Provisional Patent Application No. 60/950,080, filed Jul. 16, 2007, the entire content of the foregoing applications are incorporated by reference in their entirety.

STATEMENT REGARDING FEDERALLY SPONSORED RESEARCH OR DEVELOPMENT

This invention was made with United States Government support under Grant No. 1R43DK072560-01 by the National Institutes of Health. The government has certain rights in this invention.

BACKGROUND OF THE INVENTION

1. The Problems Known in the Art

Advances in biomaterials engineering have led to a number of highly visible and successful technologies in cardiovascular medicine and surgery, orthopedics, ophthalmology and dentistry. While the use of biomaterials has improved the quality of life for millions of people, there still remain problems with blood coagulation, fibrosis, infection, inflammatory reactions, degradation and rejection associated with currently available materials. Controlling biological interactions with materials is of great importance to the design of permanent as well as resorbable implants, cell and tissue scaffolds, and diagnostic probes, among others. The ability to control interactions between materials and bacteria is particularly important. Most materials used in medical devices are susceptible to bacterial adhesion. Once bacteria adhere to a solid surface, they generate and become embedded within a polysaccharide matrix to form a biofilm, within which, they are extremely difficult to combat. Both the host immune system and antimicrobials become less effective against the bacteria due to difficulty in penetrating the biofilm matrix and/or inactivation. In addition, bacteria in biofilms have more capacity to develop resistance to antimicrobials. To reduce morbidity and mortality due to device related infections, it is critical to prevent biofilm formation.

Catheters are routinely implanted in the bloodstream, urinary tract, chest, neck, abdomen, leg and spinal cord, and they are particularly susceptible to microbial infection, blood clotting, and occlusion that can begin within hours of implantation. An estimated ⅓ of catheters fail by infection and about ⅓ fail due to fibrin formation occluding the catheter. In either case, the most effective treatment currently is replacement with a similar device.

Implant-associated infections can result in systemic infections that in the worst-case scenario can lead to multiple organ failure and death, despite successful resolution of the original medical condition. The cost of such infections is high. For example, a single episode of central venous catheter-related bacteremia has been estimated to cost between $3,700 and $50,000 with an attributable mortality rate between 4 and 35%. Approximately 3 million central venous catheters are used each year in the United States and catheter related blood stream infections (CR-BSI) occur in over 200,000 patients with over 80,000 taking place in the intensive care unit (ICU). The cost of ICU infections alone is $296 million to $2.3 billion with between 2,400 and 20,000 deaths per year. Infection is also a major problem for dialysis patients. Over 450,000 people in the US alone have end stage kidney failure and require chronic hemodialysis. For these patients, vascular access procedures are a major cause of morbidity and mortality. AV grafts are used in about 42% of patients with an infection rate between 11 and 20%. The mortality rate due to infection of these grafts is between 12 and 22%.

Several catheter modification approaches have been evaluated for their ability to reduce the incidence of catheter-related blood stream infections (CR-BSI). The approaches can be divided into two categories. In one category, surfaces are modified to prevent bacterial adhesion. Many of these approaches involve minimization of adsorption and adhesion through steric repulsion and/or minimization of interfacial energy. In the case of catheters, adsorption of proteins, particularly fibrinogen, often leads to thrombus formation or development of a fibrin sheath and eventual occlusion. Several protein components of thrombus increase bacteria adhesion to catheters and there is an association with thrombus formation and CR-BSI. On the surfaces of hydrophobic materials, entropically driven, hydrophobic interaction dominates protein adsorption, and many research groups have shown that surfaces grafted with PEO are significantly less prone to adsorption and adhesion. Although hydrophilic coatings have been shown to reduce bacterial adhesion, problems with infection still occur.

In the second category, surfaces are modified or device materials are impregnated with agents that actively kill or prevent the growth of bacteria. Two commercially available short term catheters that fit into this category have been shown to reduce infection rates, one is chlorhexidine-silver sulfadiazine-impregnated (CSI) and the other is minocyline-rifampin impregnated (MRI). However these products pose a significant risk for developing drug resistant bacteria. This risk is lower for the antiseptic CSI catheters, but in vitro studies have found that exposure to chlorhexidine can result in increased bacteria resistance to it and other therapeutic antimicrobial agents. Furthermore, CSI is not effective if it needs to be in place for longer than three weeks, it is less effective than MRI, and serious anaphylactoid reactions associated with the use of these catheters have been reported in Japan. Although the antimicrobial catheters cost more than standard catheters, studies have demonstrated that there is an overall cost benefit of using them in high risk patients due to the high cost of treating CR-BSI. The added cost of antimicrobial catheters is between $25 and $34 per catheter, but the overall cost benefit is approximately $200 per catheter for CSI. Based on cost benefits and improved patient care, there is a strong motivation to use the antimicrobial catheters. However, these pose a very serious risk of furthering the development of resistant bacteria and are currently recommended for use only in high risk patients (in the ICU, on total parental nutrition, or immunosuppressed).

Unfortunately, these currently known technologies have not solved the needs in the art. Rather, what is needed is a material modification that (1) kills bacteria upon contact with the device such that antibacterial agents do not have to be released into the blood stream or surrounding tissue, (2) is biocompatible and will not adversely affect the patient when directly interfaced with the patient, (3) can be readily applied to a variety of materials and irregularly shaped objects, (4) prevents thrombus formation and occlusion, and (5) does not stimulate changes in bacteria that lead to resistance and therefore can be broadly used without compromising the effectiveness of clinical antibiotics.

2. Currently Known Block Copolymers

A different type of technology has been developed which uses PLURONIC® surfactants. PLURONIC® surfactants are generally high molecular weight polyoxyalkylene ether compounds that are water soluble. These block copolymer compounds have been used to immobilize bioactive entities at interfaces with good success. This approach utilizes a triblock copolymer (polyethylene oxide-polypropylene oxide-polyethylene oxide) that has been modified at the termini of the polyethylene oxide chains to allow for coupling to biomolecules. The modified copolymers are often referred to as end group activated polymers or "EGAP". Various patents and patent applications have been filed related to these types of products including U.S. Pat. No. 6,087,452, U.S. Pat. No. 6,284,503, U.S. Pat. No. 6,670,199, U.S. Patent Application Publication No. 2004/0219541, U.S. Patent Application Publication No. 2004/0142011, U.S. Patent Application Publication No. 2005/0244456 and U.S. Patent Application Publication No. 2005/0106208 (which patents/applications are expressly incorporated herein by reference). Accordingly, for additional information regarding these products, the reader should consult these patents.

The EGAP molecules self-assemble on hydrophobic materials from aqueous solutions. The hydrophobic polypropylene oxide ("PPO") center block forms a strong hydrophobic bond with the material while the polyethylene oxide ("PEO") end blocks remain freely mobile in the fluid phase. Using this approach, a thick PEO brush-like layer is formed at the material surface that serves two important purposes. First, the PEO layer acts as a cushion between the peptide and the substrate preventing any denaturing of the peptide that might otherwise result from surface interaction and retaining peptide mobility. Second, the PEO layer prevents nonspecific adsorption of proteins or cells to which the surface might be exposed in subsequent use.

Previous studies have shown that the EGAP technology has advantages over other PEO based tethering technologies: it is very simple to apply to materials by a dip coating process, it can be applied to a variety of different types of materials and irregularly shaped objects, and it provides a mechanism to systematically vary protein surface concentration. Medical devices, implants, and tissue engineering scaffolds are prepared from a number of different material types due to the different mechanical, electrical, and optical properties that different applications require. Most materials that display optimal bulk properties for a given application do not have adequate biocompatibility. Direct chemical modification of materials to improve biocompatibility is complicated and can change material properties. In some cases, direct chemical modification is not feasible based on the material type or the irregular shape of an object. Direct adsorption of biomolecules on such surfaces often leads to denaturation of the biomolecules. The EGAP technology provides a simple and versatile solution to these challenges because it can be applied to a number of different materials by a simple dip coating process and can be used to immobilize proteins and peptides with retained activity.

3. Antimicrobial Peptides

Other research has been conducted regarding antimicrobial peptides that kill or slow the growth of microbes like bacteria, fungi, viruses, or parasites. Antimicrobial peptides that have been studied include defensins, cecropins, bacteriocins, and other natural or synthetic cationic peptides. Lantibiotics are one class of bacteriocins. They include the antimicrobial peptide nisin, and are antibiotic compounds that include one or more lanthionine rings. Over 40 lantibiotics are currently known, and more are being discovered each year. Analogs of antimicrobial peptides with improved activity or stability are also being developed [1]. The unique physical structure of lantibiotics, (e.g., double bonds, thioether rings, and unusual amino acid residues), makes these antimicrobial peptides highly reactive, and different in mode-of-action from traditional antibiotics. This suggests that they may remain effective despite the global increase of resistant bacterial strains. Lantibiotics also demonstrate wide variability in their inhibitory spectrums. Some lantibiotics, (e.g., nisin and subtilin) are active against Gram-positive bacteria, while other lantibiotics (e.g., cinnamycin) are active only against Gram-positive rods. Additionally, some lantibiotics have antiviral activity, (e.g., lanthiopeptin), some function as immunosuppressors, (e.g., mersacidin), and some (e.g., duramycin and ancovenin) can inhibit biomedically important enzymes.

The structure of nisin, by far the most extensively investigated lantibiotic with reference to biomaterials applications, is shown schematically in FIG. 1. Specifically, FIG. 1 shows that the N-terminal domain (residues 1-19) includes the three lanthionine rings labeled A, B, and C. FIG. 1 also shows, the C-terminal domain (residues 23-34) includes two lanthionine rings, identified as D and E. Additionally, FIG. 1 shows that a flexible hinge region (residues 20-22) connects the two domains. (In FIG. 1 Abu refers to 2-aminobutyric acid; Dha refers to dehydroalanine; Dhb refers to dehydrobutyrine; Ala-S-Ala refers to lanthionine; and Abu-S-Ala refers to $\beta$-methyllanthionine).

Nisin has had a long history as a potent and safe food preservative. It has been demonstrated that nisin can adsorb to synthetic surfaces, maintain activity, and kill cells that have adhered in vitro. While nisin has demonstrated activity against only Gram-positive bacteria, it can be an effective inhibitor of certain Gram-negative bacteria when used in combination with other compounds such as chelating agents. *Staphylococcus aureus* and *Staphylococcus epidermidis* are the most frequently encountered biomaterial-associated pathogens, and both are Gram-positive bacteria. Nisin has been shown to prevent microbial adhesion on endotracheal suction catheters in vitro (using *Staphylococcus aureus, Staphylococcus epidermidis*, and *Enterococcus faecalis* (*Streptococcus faecalis*) as indicator organisms), prompting further studies in vivo evaluating nisin-treated intravenous (IV) catheters in sheep and tracheotomy tubes in ponies. Catheters pretreated with nisin for long-term placement (7 days) did not retain antimicrobial activity, while short-term (3-5 h) IV catheters did. The exact duration of nisin activity on IV catheters remains unknown. There were no abnormalities on clinical examination of sheep during the experimental period, and no animal in either group developed catheter-related infection or venous thrombosis. Veins with short-term catheters also showed fewer and less severe histological abnormalities compared with controls, indicating a possible protective effect on vascular endothelium. As the first-ever preclinical trial of nisin-treated implantable materials, this study represented an important step toward development of protein antimicrobial films for implantable medical devices.

Lantibiotics have many characteristics that make them valuable for biomedical applications. Unlike typical peptides, lantibiotics contain dehydrated amino acid residues with electrophilic centers that readily react with nucleophilic groups, such as bacterial DNA and enzymes. The thioether rings found in all lantibiotics make the molecules more heat stable, much less affected by reducing agents, and less reactive toward free radicals than would disulfide bonds. Lantibiotics may offer a means for preventing the rise of resistant microorganisms, and since their mechanism of action is so dissimilar to that of traditional clinical antibiotics, cross-resistance is highly unlikely. There are some reports that repeated exposure to nisin can lead to changes in bacteria that can confer some weak resistance. However, the changes that occur also appear to make the bacteria weak compared to their nonresistant counterparts and more susceptible to antibiotics or the immune response. Nisin has been used broadly and extensively in food products for many years without problems arising due to development of resistance.

There are several different mechanisms through which lantibiotics can exert their antimicrobial effect. Type A lantibiotics (such as nisin) are linear molecules that are strongly cationic. They are highly surface active and kill susceptible bacteria through a multistep process that destabilizes the phospholipid bilayer of the cell and creates transient pores. The targeted bacterium is rapidly killed by efflux of ions and cytoplasmic solutes, such as amino acids and nucleotides, and subsequent dissipation of membrane potential. The depolarization of the cytoplasmic membrane results in an instant termination of all biosynthetic processes. Structural analyses have indicated that the hydrophilic groups of nisin interact with the phospholipids headgroups, and the hydrophobic side chains are immersed in the hydrophobic core of the membrane. The "wedge" model of pore formation takes such data into account but proposes that the peptides insert into the membrane without losing contact with the membrane surface, resulting in the formation of a short-lived (i.e., duration of milliseconds to seconds) pore. In the wedge model, pore formation is proposed to be caused by local perturbation of the lipid bilayer, whereby the hydrophobic residues of the peptide are inserted shallowly into the outer leaflet of the lipid bilayer. The "barrel-stave" model on the other hand proposes that nisin binds as a monomer and inserts into the lipid bilayer. The inserted monomers then aggregate laterally to form pores. Each of these models was proposed during a time when many questions remained concerning the involvement of cell surface factors, lifetime of the pore, and number of molecules required for pore formation. These have not all been answered, but recent research has revealed the importance of the cell wall precursor "lipid II," and the functional importance of specific segments of the nisin molecule, in pore formation.

BRIEF SUMMARY OF THE INVENTION

The present invention produces surfaces, gels, foams, solutions and other products that incorporate a protein resistant component and an active antimicrobial component. It also involves the production of a surface active, antibacterial compound. The protein resistant component is a copolymer that contains one or more hydrophilic domains and at least one hydrophobic domain, such as a PLURONIC® surfactant. The protein resistant component may include an end group activated polymer (EGAP) where the end group activation site on the polymer provides the necessary link to couple an antimicrobial component, such as a lantibiotic. An antimicrobial component, such as nisin or another lantibiotic, is then tethered to the EGAP and added to the product to create an anti-bacterial surface. This approach may also be used to transform an antimicrobial compound from a relatively small entity with limited properties to an antimicrobial compound with, ampiphilic, surface active properties that may enhance the potential for adsorption, cleaning, and solubility. This new approach solves the problems of prior methods and provides the following important advantages: (1) it incorporates a natural antibacterial component to kill bacteria or other microbes, where the component is not likely to stimulate bacterial resistance, (2) it combines surface properties that will help prevent fibrin formation and occlusion, (3) it is biocompatible and can be interfaced directly with tissue, (4) it can be readily applied to a variety of materials and irregularly shaped objects, (5) based on the unanticipated results provided in the examples, the PEO chains, while inhibiting spontaneous elution as well as entrapped peptide exchange by blood proteins, also confer some degree of stability toward conformational rearrangement that is thought to translate into improved retention of activity and (5) by utilizing a natural, alternative antibiotic, it does not pose a risk for decreasing the potency of limited forms of clinical antibiotics. These advantages will allow for broader use, increased safety, and reduced medical cost.

The invention is based on the recognition that known peptides with antimicrobial activity, such as nisin, can be made to form long lasting antimicrobial surface coatings, additives, gels or foams by combining the peptide with a block copolymer, such as a PLURONIC® F108 or EGAP in a manner to form a flexible tether/and or entrap the peptide. The entrapped peptide provides antimicrobial action by early release from entrapment while the tethered peptide provides longer lasting antimicrobial protection.

One embodiment is a class of compounds with the formula:

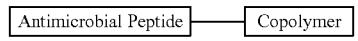

wherein the copolymer comprises one or more hydrophilic domains and at least one hydrophobic domain.

The novel, antimicrobial product formed by the present invention will have a variety of different applications and uses. Specifically, the antimicrobial product may be coated/adsorbed onto a substrate such that the block copolymer will attach to the substrate. (The way in which these block copolymers will adhere to the surface of the substrate is known in the art). Accordingly, once coated, the substrate will have an antimicrobial coating on its surface. In some embodiments, this substrate will be a medical device that may be inserted into a patient. A medical device is any type of medical device, including catheters and the like, which may be inserted into the patient or which may be used for extracorporeal treatments. In other embodiments, the substrate may be a food packaging material or a food product which will be ingested by the patient. As nisin and other lantibiotics are approved for use in the food industry by the Federal Drug Administration (FDA), this food product will be safe for consumption, but will retain its antibacterial properties. In yet further embodiments, the antimicrobial product formed in accordance with this invention will be placed in a cream, foam, powder, or gel, thereby creating a topical antimicrobial product that may applied to the skin, a wound, a surgical site or applied to the surface of a substrate/product, etc.

In some embodiments, the substrate with the antimicrobial coating will be formed in a two-step process. In the first step, the substrate will be exposed (e.g., dipped) into a solution containing the block copolymer, the end group activated block copolymer, or a mixture of the two for a time sufficient to cause the block copolymer or end group activated block copolymer to absorb/bond to the surface of the substrate. The second step will involve exposing (e.g., dipping) the block copolymer coated substrate into a solution containing the antimicrobial peptide or a functionalized form of the peptide for a time sufficient to cause the peptide to bond to the block copolymer.

BRIEF DESCRIPTION OF THE DRAWINGS

The following description can be better understood in light of several Figures, in which.

Figure 1:
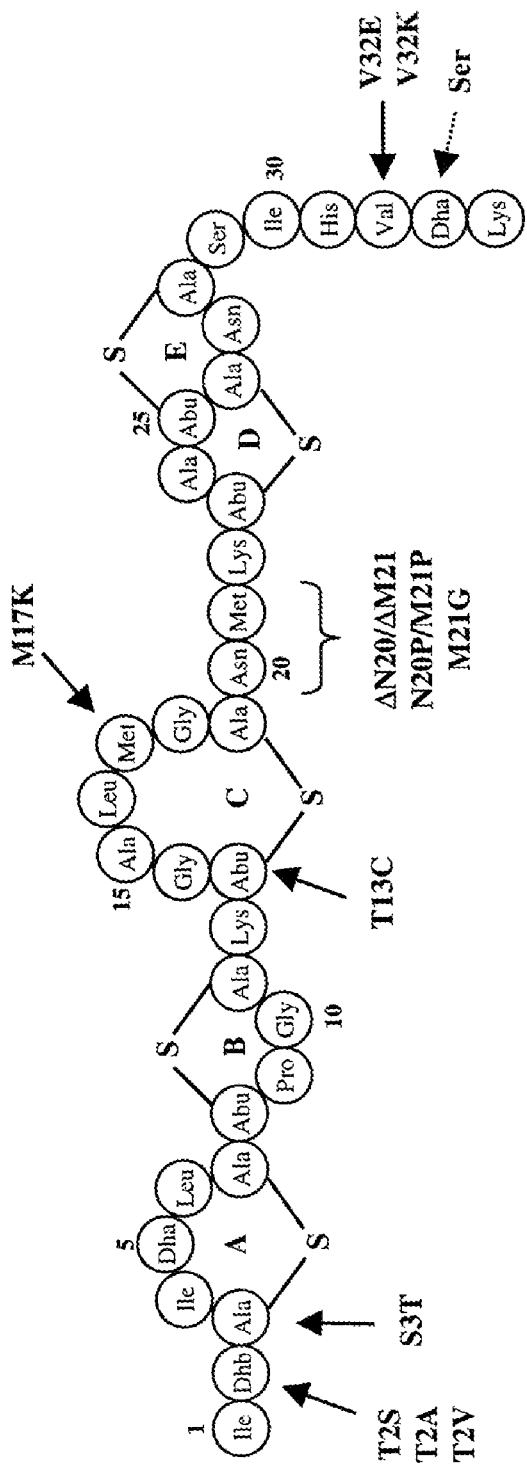
FIG. 1 schematically illustrates a representative embodiment of a nisin structure.

Together with the following description, the Figures may help demonstrate and explain the principles of the described methods and compositions.

DETAILED DESCRIPTION OF THE INVENTION

The presently preferred embodiments of the present invention will be best understood by the description herein. It will be readily understood that the components, features, and structures of the present invention, as generally described, could be arranged and designed in a wide variety of different configurations. Thus, the following more detailed description of the embodiments of the present invention, is not intended to limit the scope of the invention, as claimed, but is merely representative of presently preferred embodiments of the invention.

The invention relates to the combination of antimicrobial peptides with a block copolymer and/or an end group activated block copolymer in a manner to form a flexible tether and/or entrap the peptide. The peptide provides antimicrobial action by early release from entrapment and long lasting activity is obtained through tethered peptides.

One embodiment includes a construct of a copolymer linked to an antimicrobial peptide with the formula:

Another embodiment combines an antimicrobial peptide with an unmodified copolymer were the peptides are physically entrapped by the polymer chains of the copolymer.

Another embodiment combines the antimicrobial-copolymer construct with an unmodified copolymer and/or antimicrobial peptides where the peptides are physically entrapped by the polymer chains of the copolymers.

Yet another embodiment combines the antimicrobial-copolymer construct with an end group activated copolymer, where the end group activation site is a metal chelating group, such as a nitrilotriacetic acid group. In this embodiment, additional antimicrobial peptides may be added where the peptides are temporarily held by physical entrapment by the polymer chains of the copolymers.

The copolymers used in the preferred embodiments contain one or more hydrophilic blocks and at least one hydrophobic block. Preferred copolymer units for forming the copolymer coating of preferred embodiments include, but are not limited to, polyethylene oxide (PEO) and polypropylene oxide (PPO), PEO and polybutylene oxide, PEO and polybutadiene, PEO and poly(N-acetylethyleneimine), PEO and polyurethane, PEO and polymethylmethacrylate (PMMA), PEO and poly (s-caprolactone), PEO and poly lactide, PEO and poly (lactide-co-glycolide), PEO and polydimethyl siloxane, Poly phosphoester (PPE) and polypropylene oxide (PPO), PPE and polybutylene oxide, PPE and polybutadiene, PPE and poly(N-acetylethyleneimine), PPE and polyurethane, PPE and polymethylmethacrylate (PMMA), PPE and poly (s-caprolactone), PPE and poly lactide, PPE and poly (lactide-co-glycolide) and PPE and polydimethyl siloxane. In the preceding pairs of copolymer units, preferably, the hydrophilic domain comprises PEO. Copolymers using copolymer units of this type and their application to coating materials to prevent protein adsorption have been described previously[2; 3; 4; 5; 6; 7; 8; 9; 10] The copolymers may further comprise phenyl boronic acid.

In a certain embodiment, the copolymer comprises pendant or dangling hydrophilic domains, such as poly(ethylene oxide) (PEO) chains. The other domain(s) of the copolymer comprises a hydrophobic domain, such as a poly(propylene oxide) (PPO) chain. Additionally, in certain embodiments a linking group (R) is attached to the copolymer on one end adjacent to the hydrophilic domain to form an end-group activated polymer. For example, the end-group activated polymer may be in the form of any arrangement of the PEO and PPO blocks with the general formula:

$$(\text{R-PEO})_a(\text{PPO})_b \quad (1)$$

where a and b are integers, are the same or different and are at least 1, preferably a is between 1 and 6, and b is between 1 and 3, more preferably a is 1 to 2, and b is 1. The polymeric block copolymer has a PEO ($-C_2H_4-O-$) content between 10 wt % and 80 wt %, preferably 50 wt % and 80 wt %, more preferably between 70 wt % and 80 wt %.

The PEO chains or blocks are of the general formula:

$$-(-C_2H_4-O-)_u \quad (2)$$

where u is the same or different for different PEO blocks in the molecule. Typically, u is greater than 50, preferably between 50 and 150, more preferably between 80 and 130. The PPO blocks are of the general formula;

$$-(-C_3H_6-O-)_v \quad (3)$$

where v may be the same or different for different PPO blocks in the molecule. Typically, v is greater than 25, preferably between 25 and 75, more preferably between 30 and 60.

The copolymers may be branched structures and include other structures (e.g., bridging structures, or branching structures) and substituents that do not materially affect the ability of the copolymer to adsorb upon and cover a hydrophobic surface. Examples include the following copolymers described in the following paragraphs.

In another embodiment, the end-group activated polymer of preferred embodiments is a derivative of a polymeric tri-block copolymer with pendant R groups, as in Formula (4), below. For example, these tri-block copolymers have a hydrophobic center block of polypropylene oxide and hydrophilic end blocks of polyethylene oxide with terminal R groups, and can be represented by the formula:

$$R-(-C_2H_4-O-)_x-(-C_3H_6-O-)_y-\\(-C_2H_4-O-)_z-H \quad (4)$$

where y is between 25 and 75, preferably between 30 and 60, and x and z are preferably the same, but may be different, and are between 50 and 150, preferably 80 and 130. Certain types of polymeric surfactants are commercially referred to as "PLURONIC®" or "POLOXAMERS™", and are available, for example, from BASF.

Another suitable class of polymeric block copolymers is the di-block copolymers where a=1 and b=1, and can be represented by the formula;

$$R-PEO-PPO-H \quad (5)$$

where PEO and PPO are defined above.

Another suitable class of polymeric block copolymers is represented by the commercially available TETRONIC™ surfactants (from BSAF), which are represented by the formula:

$$(R-(O-C_2H_4)_u-(O-C_3H_6)_v)_2N-CH_2-CH_2-N\\((-C_3H_6-O-)_v-(-C_2H_4-O-)_u-H)_2 \quad (6)$$

As used herein, the terms EGAP or EGAPs refer to the block copolymers defined in Equation (1), which include the end group activated forms of PLURONICS® tri-block copolymer surfactants, the di-block surfactants, the TETRONIC® surfactants, as well as other block copolymer surfactants as defined.

As disclosed previously, a specific functional group is attached to the free end of a hydrophilic domain to form an end-group activated polymer. The specific functional group (R) may contain a member of the reactive group, such as, p-nitrophenol group, N-hydroysuccinimide group, hydrazine group, maleimide group, thiopyridyl group, tyrosyl residue, vinylsulfone group, iodoacetimide group, disulfide group or any other reactive group that is suitable for reaction with an antimicrobial peptide or a derivatized antimicrobial peptide. In certain embodiments, the reactive group is also selected from the functional groups known to be stable in an aqueous environment, such as hydrazine group, maleimide group, thiopyridyl group, tyrosyl residue, vinylsulfone group, iodoacetimide group, disulfide group. R may also comprise functional groups capable of forming ionic interactions with proteins, for example a nitrilotriacetic acid (NTA) group, which, when bound to a metal ion forms a strong bond with histidine tagged peptides or in the absence of a metal ion, may bind positively charged peptides. NTA modified PLURONICS are described in U.S. Pat. No. 6,987,452 to Steward et al., hereby incorporated by reference. R may also comprise oligonucleotides that can bind to oligonucleotide tagged proteins. Oligonucleotide modified PLURONICS are described in International Publication No. WO02/077159 to Neff et al., hereby incorporated by reference.

In a preferred embodiment, the R group comprises an R'—S—S group where R' is to be displaced for the immobilization of an antimicrobial peptide. In one embodiment, the substituent R' can be selected from the group consisting of (1) 2-benzothiazolyl, (2) 5-nitro-2-pyridyl, (3) 2-pyridyl, (4) 4-pyridyl, (5) 5-carboxy-2-pyridyl, and (6) the N-oxides of any of (2) to (5). A preferred end group includes 2-pyridyl disulfide (PDS). The reactivity of these groups with proteins and polypeptides is discussed in U.S. Pat. No. 4,149,003 to Carlsson et al. and U.S. Pat. No. 4,711,951 to Axen et al, all of which are hereby incorporated by reference. As mentioned above, end group activated polymers (EGAP)s are generally a class of composition comprising a block copolymer backbone and an activation or reactive group.

Preferred embodiments include the use of copolymer-antimicrobial constructs and/or combinations of copolymers with antimicrobial peptides for inhibiting the growth or viability of bacteria and/or other microbial agents such as viruses and fungi. The antimicrobial agent used to form the copolymer-antimicrobial construct or combined with copolymers in the preferred embodiments can be selected from the group of peptides that kill or slow the growth of microbes like bacteria, fungi, viruses, or parasites, including defensins, cecropins, bacteriocins, and other natural or synthetic cationic peptides. A preferred group of peptides is the Lantibiotics, which are one class of bacteriocin, and include nisin, subtilin, cinnamycin, lanthiopeptin, mersacidin, duramycin and ancovenin. The present application focuses on the use of antimicrobial peptides, such as nisin (and derivatives) in combination with block copolymers to create antimicrobial materials. Such materials may be applied to hydrophobic surfaces to create antimicrobial surfaces. Such products may also be used to form gels, foams emulsions etc, or added to gels, foams, emulsions, etc. Those of skill in the art will recognize that other types of antimicrobial peptides may also be used, either in conjunction with nisin and/or in place of nisin. In a certain embodiment, more than one antimicrobial peptide can be immobilized onto one surface with the use of EGAP material. The use of EGAP for protein immobilization has been described previously by Caldwell and others. However, Caldwell and others used EGAP to prepare surfaces for the purpose of evaluating or promoting specific protein-protein interactions and cell adhesion to surfaces [11; 12; 13; 14; 15].

Lantibiotics are available from a variety of different sources. For example, a nisin-producing strain of *Lactococcus lactis* is available at a laboratory run by Dr. Joseph McGuire at Oregon State University in Corvallis, Oreg., USA. Effective purification methods for this product involve treatment of cell-free supernatants by hydrophobic interaction chromatography followed by reversed phase HPLC using aqueous acetonitrile and 0.1% trifluoroacetic acid as eluents, as described elsewhere. Culture supernatants for this purpose are obtained (after growth in MRS broth at 30° C. for 24 h) by centrifugation, pH adjustment and membrane filtration. In general, production and purification of lantibiotics are well documented in the literature, including enhancements to the fermentation media (e.g., supplemental phosphate, serine, and threonine, coupled with broad spectrum protease inhibitors) to increase yields. Nisin is also available commercially. For example, NISAPLIN® (which is sold by the SIGMA-ALDRICH Company of St. Louis, Mo., USA) is available as a food-grade preservative with the following composition: nisin (2.5%); NaCl (77.5%); protein (mainly denatured milk proteins, 12%); carbohydrate (6%); water (2%).

The coupling of the antimicrobial peptide to the block copolymer may be achieved using a variety of methods. As explained herein, the lantibiotics may be attached to the end group activated block copolymers through disulfide linkages. Accordingly, the lantibiotics may be modified to include a thiol group, so that this disulfide linkage may be made. With respect to nisin, this modification may occur by chemically introducing a thiol group to the N-terminal isoleucine of the nisin peptide. Those of skill in the art will recognize that in other antimicrobial peptides, a similar modification may be made to an N-terminal amine or other amines, for example, on lysine residues, in the peptide. The block copolymers also contain an activated end group in which one or more of the hydroxyl end groups of the PEO groups have been replaced with pyridyl disulfide moieties. Accordingly, the thiolated nisin may then be linked to the block copolymer by having the thiol group of the nisin bond (via disulfide linkages) to the pyridyl disulfide moieties of the block copolymers. Another method involves the use of recombinant protein engineering techniques to introduce a moiety that can be used to bond the antimicrobial peptide to EGAP. For example, a recombinant form of nisin may be produced that contains a c-terminal or n-terminal cysteine residue. In some cases, the cysteine residue may be separated from the native sequence of the peptide by a glycine spacer. Accordingly, the cysteine terminated peptide may then be linked to a pyridyl disulfide activated block copolymer through a disulfide exchange. Another method involves selecting a form of the end group activated copolymer that is capable of reacting directly with the native form of nisin. This method can be achieved by reacting a p-nitrophenol activated copolymer or an N-hydroxysuccinimide activated copolymer with the N-terminal amine of nisin. Yet another method involves the production Nisin that is recombinantly engineered to produce a form of the peptide having a terminal histidine tag. A histidine tagged antimicrobial peptide could then be bound through very strong ionic interactions, in the presence of divalent metal ions, to a block copolymer that has an activated end group in which one or more of the hydroxyl end groups of the PEO groups have been replaced with a nitrilo triacetic acid group. These antimicrobial constructs may then be separated from any unreacted nisin by chromatography or dialysis and may be used as antimicrobial agents against bacteria or other microbes.

Other ways and/or methods for introducing the thiol group or other reactive groups may be used and will depend (in part) on the particular lantibiotic being used. Further, with respect to other types of activated end groups that may be introduced to block copolymers, other modifications/chemical groups may be added to the lantibiotics in order to ensure coupling between these two molecules, as will be recognized by those of skill in the art.

Specific examples will be given herein regarding the reaction conditions which will bond and/or bind the block copolymer and the lantibiotic (e.g., the reaction conditions necessary to create the disulfide linkages between the block copolymer and the thiol containing lantibiotics). However, once this connection has been formed, an antimicrobial product will be formed that will have a variety of different applications and uses. These coatings also effectively prevent thrombus formation on a surface. Thrombus formation and antibacterial activity are two of the most important problems that occur for vascular devices and these problems often occur in combination. Accordingly, a few possible applications of the coatings of the present embodiments are given below.

For example, medical devices may be coated with this antibacterial coating including drug delivery pumps, drug reservoirs, encapsulation devices (for cells, drugs, or biologics), vascular access devices, transcutaneous devices, neural stimulation devices, neural intervention devices, intubation tubes, sutures and other wound closure devices, shunts, drainage tubes, feeding tubes, orthopedic devices, dental devices, extracorporeal circulation devices and filtration devices, tubing, fittings, luer locks, optical devices, and/or other medical devices which are inserted into the patient's body or which come into contact with the body or body fluids.

It has been shown that PLURONICS can be coated onto certain cells or tissues, for example, PLURONICS have been coated onto red blood cells to make a universal blood donor supply. These EGAP-nisin or F108-nisin antibacterial coatings on tissue products could provide a benefit. One example would be coated heart valves. Today, bacterial infection is a major problem associated with heart valve replacement. Because of this, many surgeons will dip tissue heart valves in a solution of vancomycin in the operating room ("OR") before implanting the valve. This is problematic because (1) there is no consistency, (2) it adds a step in the OR, (3) it raises the potential to develop bacterial resistance to vancomycin, which is one of the world's most important clinical antibiotics, and (4) it does not enable patient tracking to determine what the actual benefit of applying the antibacterial agent to the valve is in terms of patient outcomes. A valve that was precoated with EGAP-nisin would be a superior product that would overcome these problems. Furthermore, the PEO component of the coating may also provide a benefit in terms of reducing calcification of the valve. These benefits could potentially apply to many other types of tissue products as well.

In other situations, coating storage containers with EGAP-nisin constructs to (1) reduce the chance of bacterial infection without adding an antibiotic to the product, (2) reduce the degree of protein denaturation in blood or biologics (for research or pharmaceutical applications), and (3) reduce protein degradation that occurs due to release of proteases from bacteria. Such storage containers might be used for food packaging, blood bags, proteins or pharmaceuticals.

Solutions for cleaning medical equipment, items in antiseptic or sterile environments, or food preparation equipment/environments (cleaning and short term protection), are also possible applications of the present antibacterial coatings.

Solutions for coating personal products or industrial products are another type of potential applications. For example, mouth guards for sporting activities, orthodontic devices (retainers, dental mouth pieces (mouth guards to prevent teeth clenching)), face or breathing masks, pacifiers, contact lenses, adult products, food preparation surfaces, food, food packaging, reusable water containers (such as for camping, sports hydration systems, water bottles, etc., computer keyboards, telephones, rental car steering wheels, health club equipment, whirlpool spas, humidifiers, decorative fountains, and hot water tanks may all be coated with the products of the present embodiments to provide antimicrobial properties. Cooling towers, whirlpool spas or steam baths at hotels, gyms or spa centers, as well as filtration devices and water lines (especially those used in dental clinics, dialysis centers, hospitals, and aseptic or sterile manufacturing or packaging areas (for example recombinant protein manufacturing, biopharmaceutical manufacturing or pharmaceutical packaging)).

Moreover as both PLURONIC® F108 and nisin are approved as food additives, the present embodiments may be used in the food industry, compared to other approaches like washing with alcohol, rinsing with bleach-water or washing with soap, the block copolymers containing nisin will provide a lasting antimicrobial activity. For night guards and retainers, the antibacterial coatings may even help prevent tooth decay because people usually wear these products all night.

One method of using the invention includes obtaining a dry powder comprised of either a block copolymer and nisin or EGAP-nisin construct. The user adds the dry powder to water and then incubates the desired product or surface in the solution for a given time period (the time period would likely be 30 seconds to 30 minutes) and then rinses with water. The present embodiments also include prepared solutions containing either the block copolymers-nisin construct or a mixture of block copolymer and nisin into which the user dips the item in for some time period (for example 30 second to 30 minutes) and then rinses with water.

Wound healing gels are yet another application of the present block copolymers-nisin products. For examples, PLURONICS have very useful properties in terms of sol gel transitions. At certain concentrations, certain PLURONICS or mixtures of PLURONICS will form micellar solutions or gels. Hydrophobic entities like nisin will often be trapped in the hydrophobic core of such micelles or polymer structures within such gels. The gels are biocompatible and have high water content so they would be well suited for protecting wounds. These gels could be combined with growth factors to promote healing while providing protection for wounds. These gels may be combined with anti-inflammatory agents to prevent scarring while providing protection for wounds. Such gels would be especially useful for diabetic ulcers and burns.

Foam cleaning solutions could also benefit from the inclusion of the present antimicrobial compounds. Specifically, if the PLURONICS are modified as taught herein, these compounds could be added to the cleaning solution to provide antimicrobial properties to the product.

Further, PLURONICS have been previously used to prevent surgical adhesions. Again, if these PLURONICS are modified as taught herein, antibacterial properties will be obtained. Addition of block copolymer-nisin constructs to either toothpaste or mouth wash may provide lasting protection from tooth decay (possibly 1 to 10 hours depending on when a person brushes or uses mouth wash and eats).

It should also be noted that the present block copolymer-antimicrobial compounds may also be used in conjunction with metal chelating agents. Specifically, one or more of the block copolymers, instead of containing an antimicrobial agent, may instead include a metal-chelating agent at its termini. These types of metal chelating block copolymers are taught in U.S. Pat. No. 6,087,452 (which has been incorporated herein by reference). The spectrum of organisms (bacteria) susceptible to nisin and other lantibiotics can be broadened to other species when the lantibiotic (nisin) is used in combination with other compounds, such as chelating agents. Some chelating agents can make the bacteria more vulnerable to the lantibiotic and/or other antibiotics. This combination of an antibacterial block copolymer and a chelating agent may be achieved by coating a surface with a combination of EGAP-nisin and EGAP-NTA, where NTA is the strong metal chelator, nitrilo triacetic acid. An advantage of this approach is that the metal chelating agent is tethered to the substrate and therefore would not be released into the surrounding environment, which may be blood or tissue. In many cases anti-thrombotic and anti-proliferative functions, as well as anti-infective functions, are desirable characteristics for a biomaterial. Accordingly, in some embodiments, the combination with a metal chelating agent may be desirable.

For certain applications that require longer term stability, it may be necessary to incorporate additional yet practical steps in the coating process to create longer term stable layers that are either physically entrapped or covalently bound to a surface as described below.

One approach that has been described previously involves the use of pretreatment with a silane and subsequent irradiation to covalently bind EGAP to metal or glass substrates. Studies using rigorous washing with sodium dodecyl sulfate (SDS) indicate that this approach increases the stability of both EGAP and PLURONIC® coatings on surfaces, while retaining the protein repelling benefits of the PEO component of the coating. This grafting technique is also amenable to a wide variety of biomaterials, both organic and inorganic. Another approach involves the use of coadsorbed heat or UV activatable crosslinkers, such as dicumyl peroxide (DCP), to produce more permanent coatings by crosslinking the copolymers to the underlying substrate. DCP has been investigated by others for incorporating PLURONICS in bulk polymers used for blood bag materials with good success. Another approach would involve matrixing the EGAP-antimicrobial construct with the bulk polymer from which a device is to be made prior to extrusion or molding.

The antimicrobial block copolymers may be made in accordance with a variety of different methods. For example, some embodiments may be constructed in which the substrate surface is first coated with the end group activated block copolymer. This may occur by exposing (such as by dipping) the substrate into a solution of the end group activated block copolymer. Then, in a second step, the substrate surface is exposed (i.e., sprayed or dipped) with a solution of the antimicrobial peptide or derivativized antimicrobial peptide for a time sufficient to cause the peptide to covalently bond to the end group activated copolymer.

In other embodiments, the antimicrobial coating may first be produced by reacting the end group activated block copolymer with the antimicrobial peptide or derivatized antimicrobial peptide. Depending on the reaction conditions, subsequent processing steps, and the final product application, the step of purifying the lantibiotic containing block copolymer may or may not be necessary. After the lantibiotic containing block copolymer has been formed, a solution of this product will then be applied to the surface of the substrate (by dipping the substrate into a solution, spraying a solution of the lantibiotic containing block copolymer onto the top of the surface, etc.).

Although much of the discussion herein focuses on covalently linking the lantibiotic to the block copolymer, other research has indicated that such covalent linking is not strictly necessary. Research has indicated that when a surface was coated with PLURONIC® F108 and incubated with nisin, the PLURONIC® F108 held the nisin on the surface and released it slowly with washing. Although not being limited by this theory, it is believed that a substantial amount of nisin gets temporarily entrapped in the PEO chains of this copolymer and that there might be specific physical interactions between nisin and the PEO chains that promote the entrapment. Moreover, such a layer may "protect" nisin from possible surface exchange by blood proteins and may also help prevent loss of activity due to denaturation. Indeed, circular dichroism data indicate that PEO entrapped nisin retains greater activity compared to directly adsorbed nisin. The entrapped nisin is slowly released from the block copolymer over time (and through washing). This slow release of the entrapped nisin gives the surface an antibacterial property, which will be lost once all of the nisin has been released from the surface and is no longer in the proximity of the device. Therefore, using this knowledge, it is possible to prepare surfaces that have antibacterial activity over relatively short time periods compared to the covalently bound nisin using only PLURONIC® F108 (or other block copolymers) and nisin for certain applications. This approach would also require fewer steps and fewer reagents to apply the coating to surfaces and therefore would also provide an advantage in terms of manufacturing cost, time and requirements for equipment.

It should be noted that the ability of the PLURONIC® to entrap nisin was highly unexpected and contrary to the general knowledge in the art. It is well known that PEO resists protein interactions and PEO and PLURONIC® F108 coated surfaces have been shown to prevent protein adsorption. Therefore, prior to applicant's research, it was believed that nisin would not interact with the PLURONIC®, other than at the reactive site on end group activated PLURONICS Thus, the finding that the nisin is entrapped in the PLURONIC® surface coatings at locations other than the reactive end site is unexpected.

Further research has indicated that EGAP coated substrates may have better protein repelling properties than PLURONIC® F108 coated substrates when either UV or e-beam irradiation was used to "permanently" bind the triblock copolymers to surfaces. Although not limited by this theory, it is possible that some degree of crosslinking between either the polymer itself or the polymer and the surface (through the end group active sites) results in a more effective protein repelling layer. If there is a crosslinked network on the surface, it is possible that this layer may act as a better entrapment layer for the antimicrobial agent compared to F108 alone, and will improve the ability of the surface to entrap antimicrobial agents.

The ability of block copolymers to entrap nisin and other lantibiotics means that embodiments may be constructed which have a quantity of entrapped lantibiotics and another quantity of lantibiotics covalently attached to the block copolymer. These surfaces provide early release and antibiotic protection from the entrapped nisin (or other antimicrobial agents) as well as longer acting protection from surface attached nisin.

Those of skill in the art will realize that, in addition to nisin, other molecules, including peptides, drugs, therapeutics, or other biological compounds may be entrapped within the block copolymers. For example, embodiments may be made in which peptides, drugs, DNA sequences, siRNA, etc. may be entrapped in the block copolymer and then slowly released. If the surface of the substrate is a medical device that is inserted into the human patient, it may be desirable to have these compounds slowly release the compounds into the patient's body as it provides a new and in improved way of introducing medicines, therapeutics, etc. into the patient.

Non-limiting examples will now be given regarding the preparation and research that has been done with nisin and/or one or more block copolymers. As noted above, those of skill in the art will recognize that other types of lantibiotics, other than nisin, may be reacted in the same manner.

Example 1

Preparation and Analysis of Coated IV Catheters
Substrate Coating:
IV catheters (24G×¾", Terumo) were cut at the base and then heat sealed using a Bunsen burner on either ends. The length available for study was 1.9 cm. Samples were prepared as indicated for n=4. Controls: (1.) Sample with No bacteria, (2.) Samples uncoated, (3.) Sterile phosphate buffer, 10 mM, pH6.0 (PB) treated samples, (4.) F108 (1% w/v) coated, (5.) EGAP-NTA (1% w/v) coated samples. (Other than 1 all others had bacteria culture). Samples under study: Nisin coated, F108 with Nisin coated and EGAP-NTA with Nisin coated. The nisin concentration was 0.5 mg/ml.

All the samples were rinsed with 1× $H_2O$ and the appropriate samples were coated with respective polymers in 1% w/v solution in sterile water overnight. The samples to be further treated with nisin and a control were then rinsed 3 times with PB.

Nisin Preparation: Nisin was dissolved in monobasic potassium phosphate. Dibasic potassium phosphate was then added to attain final pH of 6.0 and a concentration of 10 mg/ml. The nisin stock solution was then filtered using a 0.2 µm, low protein binding filter, and diluted to the required concentrations using PB. The Nisin solutions were added to the appropriate samples and coated overnight. All the samples were then rinsed 3 times with PBS (20 mM PB, 150 mM NaCl) irrespective of the type of coating/treatment.

Bacteria Culture and Incubation with Samples:

*Pediococcus Pentosaceus* FBB61-2, a gram positive bacterium, was used as a sensitive indicator strain. A glycerol stock solution of *P. Pentosaceus* was streaked on an agar plate and grown for 24 hrs in a 37° C. incubator. Single colonies of the bacteria where picked and inoculated in 2 separate 10 ml aliquots of MRS (de Man, Rogosa and Sharpe) broth solution in 50 ml polystyrene tubes. A control plate was also prepared with just the loop wire streaked on the surface which had undergone the same sterilization procedure as that needed for bacteria. The control too was inoculated into 10 ml of MRS broth. The controls and the two samples were grown overnight on a shaker plate at 250 rpm. A spectrophotometer analysis of the samples and the control was performed and the respective samples were diluted using MRS broth to obtain an absorbance value of ~0.1 at 600 nm. One ml aliquots from the two diluted bacteria culture samples and the control were added to the coated samples in 1.5 ml polystyrene tubes.

Biofilm Analysis:

The bacteria cultures were incubated with samples and controls at 37° C. under static conditions for 24 hours. The culture solutions were removed and all the samples were rinsed 3 times with PBS and placed in new, sterile 1.5 ml polystyrene tubes. One ml of MRS broth was added to all the tubes containing the samples and then the samples were sonicated for 25 min. Post sonication, the samples were placed in a 37° C. incubator. Samples were removed after 4 hrs of incubation and placed in a 4° C. refrigerator in order to retard the growth of bacteria. However, at this time point, it was found that there was no measurable difference between the uncoated controls treated with and without bacteria. Therefore, all the samples were placed back in the 37° C. incubator to be studied after a longer time period. The duration of the second incubation period was 14 hours, after which, samples were placed in a 4° C. refrigerator in order to retard the growth of bacteria. Spectrophotometer analysis was done with the Blank solution being MRS broth at 4° C.

Figure 2:
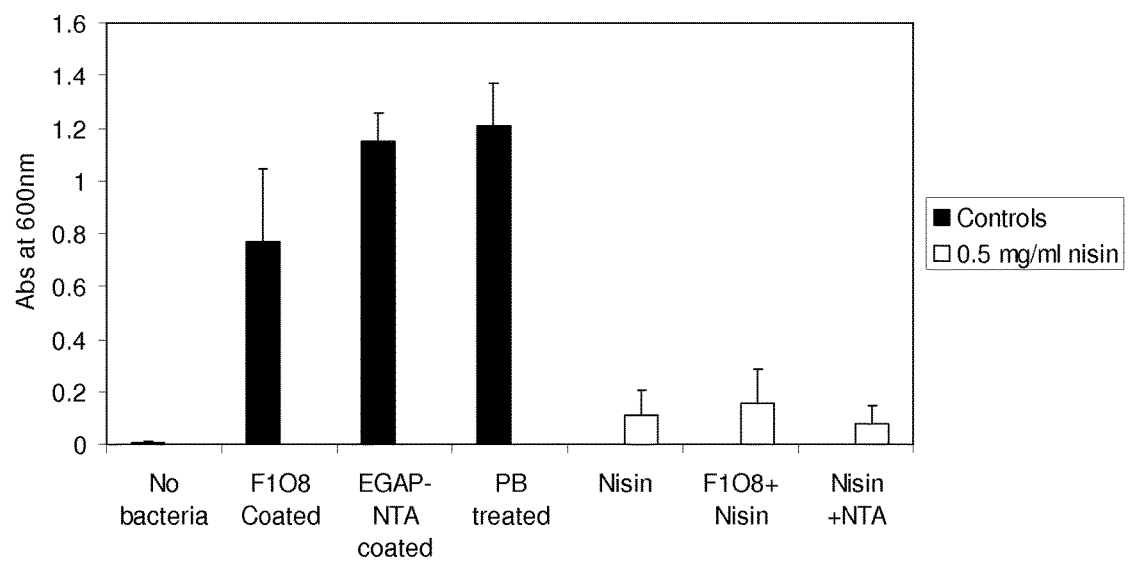
FIG. 2 contains a graph depicting experimental results of bacterial growth and attachment on IV catheters that were uncoated or coated with PLURONIC® F108, EGAP-NTA, Nisin, F108+Nisin, or Nisin+NTA.

Results:

The results of the experiment in Example 1 are displayed in FIG. 2 and indicate that less bacteria adhere to and grow on substrates coated with nisin, F108 and nisin, or EGAP+NTA and nisin. Specifically, FIG. 2 illustrates *Pediococcus Pentosaceus* attachment and growth on polyurethane IV catheters that were uncoated (PB treated), coated with F108 (F108 Coated), EGAP-NTA, Nisin, F108+Nisin, and EGAP-NTA plus nisin (Nisin+NTA).

Example 2

Duration of Activity of Coated Substrates

Substrate Coating:

Three variables were evaluated in this experiment:
1. the effect of combining a polymer coating with nisin
2. the effect of repeatedly challenging surfaces with fresh bacteria cultures over time versus a single incubation with bacteria followed by incubation in MRS
3. incubation time (3 or 7 days)

Polymer Coating:

Polystyrene 24 well plates (sterile, non-tissue culture) (Falcon, Becton Dickenson) were rinsed with sterile diH2O and to the appropriate wells a 1% w/v sterile filtered solution of F108 or EGAP-NTA was added. The plates were placed on a shaker assembly at 250 rpm overnight.

Nisin Solution Preparation:

Nisin stock solution at concentration of 10 mg/ml in 0.1% trifluoroacetic acid (TFA) was dissolved in a solution of 0.1M monobasic, 0.1M dibasic potassium phosphate, 10 mM EDTA and diH2O to obtain a final concentration of 100 µg/ml at pH 6.8.

Nisin Coating:

The wells to be coated with nisin were rinsed 3 times with diH2O and 350 µl of nisin solution was added to the designated wells. The plates were placed at ambient temperature under dark conditions on a plate shaker at 250 rpm over night.

Bacteria Culture Preparation:

A glycerol stock solution of *P. Pentosaceus* was streaked on two agar plates and grown for 24 hrs in a 37° C. incubator. A single colony was picked from each of two agar plates and inoculated in 2 separate 15 ml aliquots of MRS broth solution in 50 ml polystyrene tubes. A control plate was also prepared with just the loop wire streaked on the surface which had undergone the same sterilization procedure as that needed for bacteria. The control too was inoculated into 15 ml of MRS broth. The control and the two samples were grown overnight on a shaker plate at 250 rpm. The absorbance of the *P. Pentosaceus* cultures and controls were measured using a spectrophotometer. The cultures were diluted using MRS broth to obtain an absorbance value of 0.1 at 600 nm. Bacteria samples prepared and diluted in this way will be referred to as the standard bacteria solution. In this experiment, a subset of samples was treated with fresh bacteria at multiple time points. For each time point, a fresh standard bacteria solution was prepared as described above.

Sample Treatments:

Initial Treatment with Bacteria:

The coating solution was removed and aliquots of 350 µl of the standard bacteria solution were added to the wells. For certain control samples, MRS was added instead of the standard bacteria solution.

Secondary Treatment—Bacteria:

After the initial bacteria treatment, the previous culture was removed and without rinsing, fresh standard bacteria solution was added to the sample wells. At the specified time point, the bacteria culture was removed from the wells and rinsed 3 times with 1 ml of sterile diH2O. Fresh MRS (350 µl) was then added to the wells and incubated for 24 hours. The broth was removed from samples and diluted to 1/10th, 1/20th and 1/40th with fresh MRS broth and the absorbance of each dilution was measured at 600 nm.

Secondary Treatment—MRS:

After the initial bacteria treatment, the bacteria culture was removed and rinsed 3 times with sterile diH2O (1 ml). Fresh MRS broth (350 µl) was added to these wells. At the specified time point, the MRS broth was removed and the samples were washed three times with diH2O. Fresh MRS broth (350 µl) was then added and incubated with the samples for 24 hours. The MRS broth was removed from samples and diluted to 1/10th, 1/20th and 1/40th with fresh MRS broth and the absorbance of each dilution was measured at 600 nm.

Results

Figure 3:
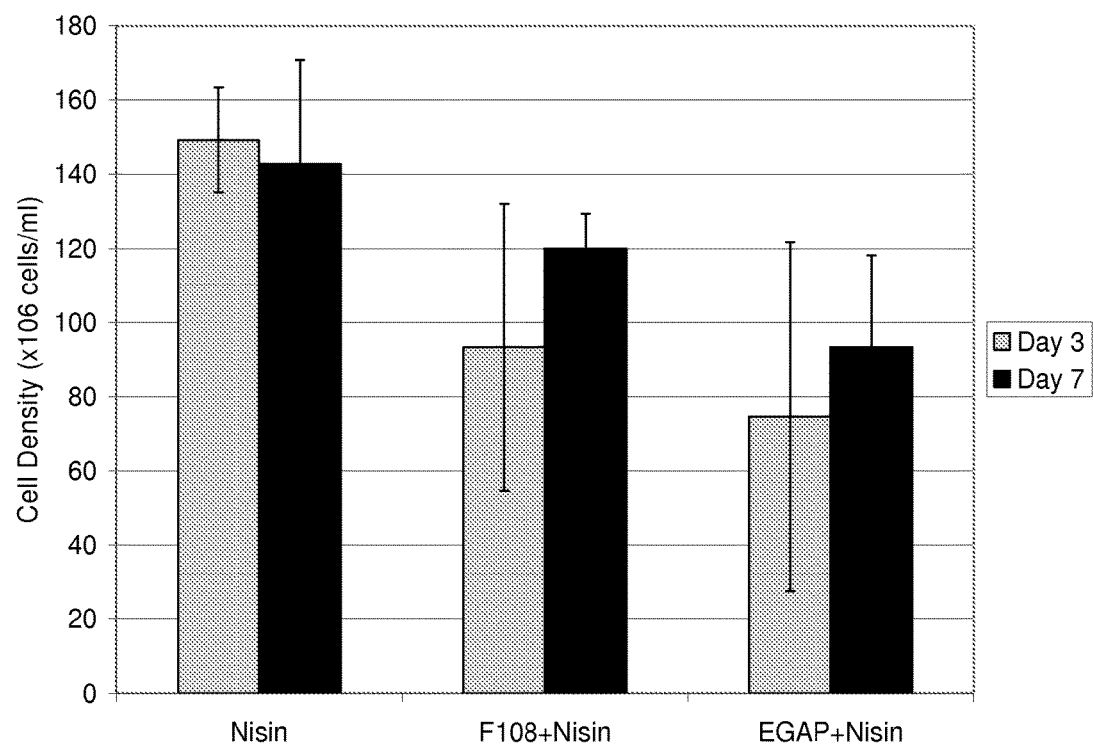
FIG. 3 contains a graph depicting experimental results of bacterial growth and attachment on substrates that were coated with Nisin, F108-Nisin, or EGAP+Nisin and were also exposed to a standard bacterial solution for 1 day followed by a rechallenge with fresh bacteria for 3 or 7 days.

The results are shown in FIG. 3 for the samples having the secondary treatment with bacteria. In particular, as discussed above, FIG. 3 shows *Pediococcus Pentosaceus* attachment and growth on substrates exposed to a standard bacteria solution for 1 day followed by rechallenge with fresh bacteria for 3 or 7 days. In FIG. 3, PS coated with nisin only is referred to as (Nisin), PS coated with F108 and nisin is referred to as (F108+Nisin), and PS coated with EGAP-NTA and nisin is referred to as (EGAP+Nisin).

Figure 4:
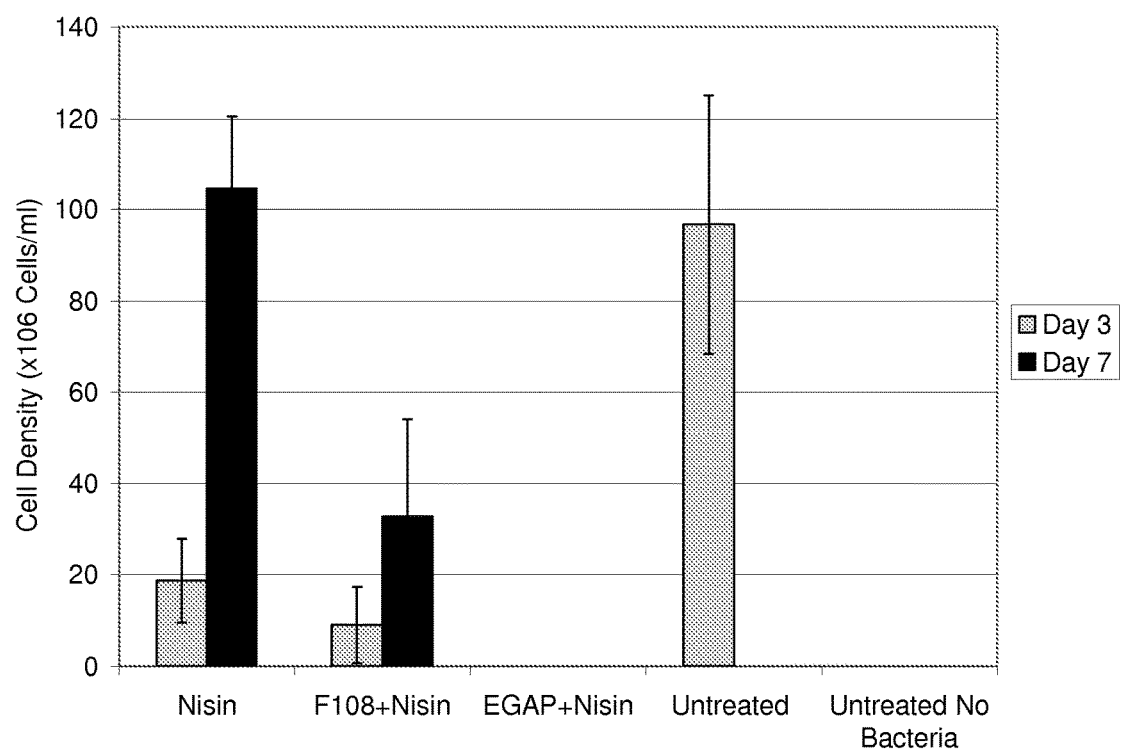
FIG. 4 contains a graph depicting experimental results of bacteria attachment and growth on substrates that were coated with nisin only, F108+Nisin, or EGAP+Nisin; controls include uncoated polystyrene and uncoated polystyrene that was treated with MRS broth only; the substrates were also exposed to a standard bacterial solution for 1 day followed by MRS broth for 3 or 7 days.

The results are shown in FIG. 4 for the samples having the secondary treatment with MRS. As stated, FIG. 4 shows *Pediococcus Pentosaceus* attachment and growth on substrates exposed to a standard bacteria solution for 1 day followed by MRS broth for 3 or 7 days. In FIG. 4, PS coated with nisin only is referred to as (Nisin), PS coated with F108 and nisin is referred to as (F108+Nisin), and PS coated with EGAP-NTA and nisin is referred to as (EGAP+Nisin). Uncoated polystyrene (Untreated) and uncoated polystyrene that was treated with MRS broth only (Untreated No Bacteria) were used as controls. For control samples, data is only shown for the Day 3 time point.

Example 3

Activity of Nisin on Microspheres in the Presence of Serum

The antimicrobial activity of nisin coated microspheres was compared to that of microspheres coated with a combination of PLURONIC® F108 and nisin after incubation with horse serum for 7 days.

Preparation of F108-Coated Surfaces.

Polystyrene microspheres (1.247 μm diameter, Part No. 81002497100290, Seradyn) were mixed with F108 (5 mg/mL) and incubated in phosphate buffer overnight on a rotator. The hydrophobic PPO block of the F108 molecule adsorbs on the polystyrene surface such that the hydrophilic PEO chains extend into the solution phase. Unbound F108 was removed from coated microspheres by repeated washing, including vortexing and sonication, centrifugation and re-suspension in phosphate buffer.

Nisin Loading and Incubation.

The F108-coated and bare microsphere samples were independently mixed with $8 \times 10^{-3}$ mg/ml nisin and incubated in phosphate buffer for 1 h on a tube rotator at room temperature. Unbound nisin was then removed by repeated washing (sonication, centrifugation and re-suspension in phosphate buffer). The absence of unbound nisin in the supernatant was verified by application of an agar plate diffusion assay [3, 4] on a plate seeded with *Pediococcus pentosaceus*. The agar diffusion assay is the most common type of nisin activity assay. In brief, holes were aseptically punched in a nutrient agar plate seeded with *P. pentosaceus*, and samples of supernatant were placed into the wells. After incubation, zones of inhibition about each well were recorded. Microsphere suspensions were used only after detecting no nisin activity in the supernatant (i.e., no visible inhibition zones around the wells) after the final wash step. Nisin ($8 \times 10^{-3}$ mg/mL) was also incubated in microsphere-free phosphate buffer (10 mM) and F108 (5 mg/mL) solutions for controlled comparison. The nisin-loaded microsphere and control samples were then incubated in phosphate buffer or equine serum of desired dilution (10, 50 and 100% serum) for desired periods of time (0, 1, 4, and 7 days) at 37° C.

Cultivation of *P. pentosaceus* and Measurement of Antibacterial Activity.

MRS broth was used for cultivation of the nisin-sensitive *P. pentosaceus* strain FBB 61-2. MRS (52.2 g, Cat. No. 1.10661, EMD Chemicals, Inc.) was dissolved in 1 L of DI water and autoclaved at 121° C. for 30 min. *P. pentosaceus* was incubated overnight (20 h) at 37° C. and placed on an orbital shaker at 220 rpm. The optical density ($OD_{600}$) of the overnight culture, and a 100-fold dilution of the overnight culture, was measured to ensure consistency of cell density.

After incubation of samples in either buffer or equine serum, microspheres were washed twice then mixed with a 100-fold dilution of overnight *P. pentosaceus* culture at 37° C. for 4 h. These were sampled and diluted 100-fold. Culture samples (0.5 mL) were then evenly dispersed with MRS-based melt agar (44° C.) on Petri dishes. The dishes were incubated at 37° C. for 48 h, until bacteria colonies became visible. The number of colonies recorded after 48 h was taken as an indication of the potency of the nisin coatings during the period of suspension with *P. pentosaceus*.

Figure 5:
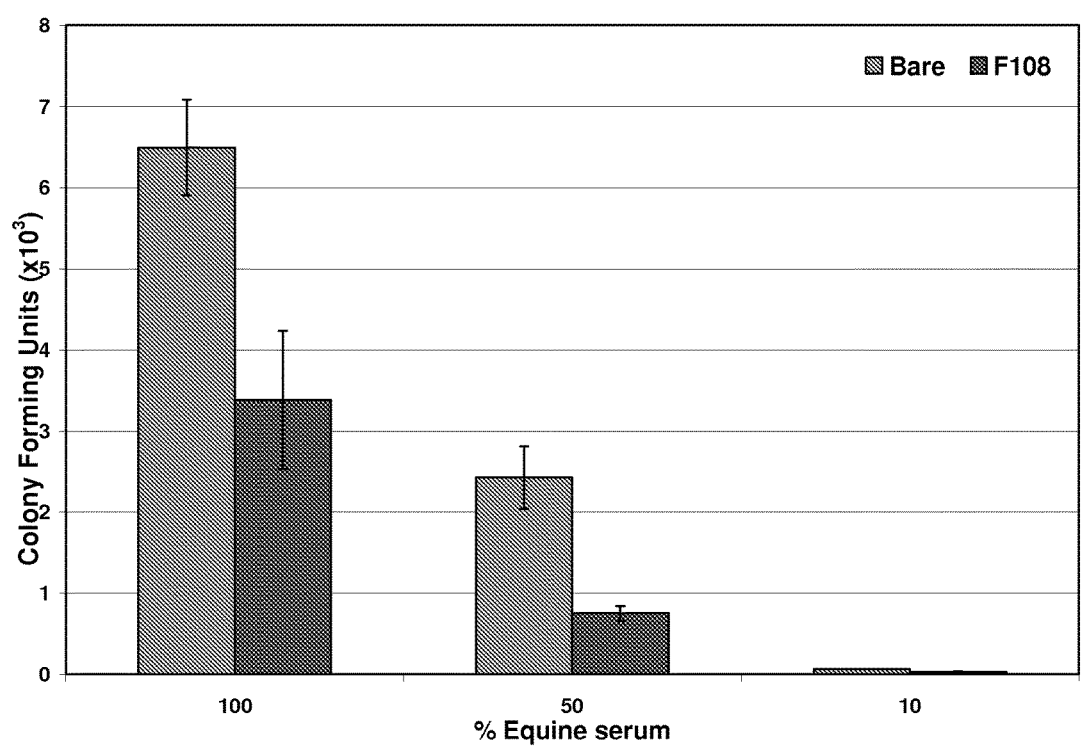
FIG. 5 contains experimental results depicting the antimicrobial activity of microspheres contacted with nisin and incubated in horse serum for 7 days.

FIG. 5 shows the results of the comparison of antimicrobial activity between uncoated and F108-coated microspheres, after contact with nisin and incubation with equine serum at 37° C. for 7 days. While an increase in serum protein concentration reduced the activity of nisin retained on the microspheres in each case, the F108-coated microspheres clearly retained more nisin activity than the bare microspheres, when challenged by blood proteins. As above, these results indicate that the F108 coating inhibits exchange of nisin by blood serum proteins.

Example 4

Nisin Adsorption and Elution on Bare or Pluronic® F108 Coated Silanized Glass

Ellipsometry was used to measure the relative rates of adsorption and elution of nisin from bare hydrophobic or PLURONIC® F108 coated silanized, silica surfaces. Ellipsometry was performed as follows.

A silica sample (coated with F108 or uncoated) was placed into a fused quartz, trapezoid cuvette (Hellma Cells, Germany) which was secured on the sample stage of an automatic in situ ellipsometer (Model L-104 SA, Gaertner Scientific Corp.) modified to allow for stirring and flow. After 4.5 mL of 10 mM phosphate buffer (pH 7.0) was injected into the cuvette, the ellipsometer stage was adjusted to obtain a maximum in reflected light intensity and steady optical properties. Surface optical properties were recorded every 15 s for 30 min before 0.5 mL of protein or F108 solution was injected into the cuvette to yield a final protein concentration of 0.50 mg/mL, or final F108 concentration of 0.5% (w/v). Adsorption was allowed to occur for a desired period of time, after which the surface was rinsed in situ with 10 mM sodium phosphate buffer at a flow rate of 31.6 mL/min for 5 min. Film properties were then monitored for a desired "incubation" period. Any additional protein adsorption and rinsing-incubation steps carried out in a given experiment were performed in the same manner described above.

A one-film-model ellipsometry program [19] was used to determine the adsorbed mass of protein from the ellipsometrically determined values of film thickness and refractive index (these optical properties being determined simultaneously at each measurement) according to Cuypers et al. [20]. A partial specific volume of 3.837 mL/g and a molecular weight to molar refractivity ratio of 0.729 g/mL were used.

Each experiment was performed at least twice on each type of surface, with an average deviation from the mean of about 0.005 μg/cm$^2$.

Figure 6:
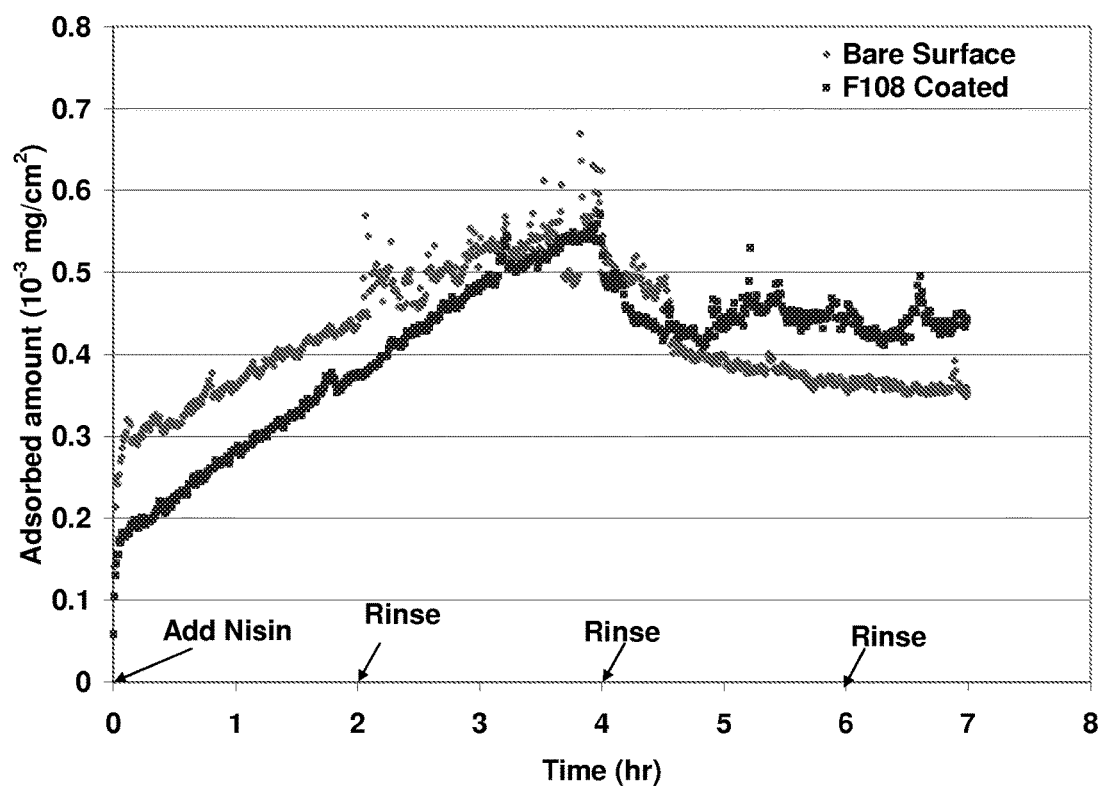
FIG. 6 contains experimental results depicting a comparison of nisin adsorption and elution kinetics at bare hydrophobic and F108-coated surfaces.

The results shown in FIG. 6 provide a representative comparison of nisin adsorption and elution kinetics at bare hydrophobic and F108-coated surfaces. Nisin adsorption did not reach a plateau in either case, and based on dimensions of nisin in solution (if modeled as a cylinder, about 2×5 nm) a monolayer of molecules adsorbed "side-on" (i.e., in an area equal to 2×5=10 nm$^2$) and "end-on" (i.e., in an area equal to 2×2=4 nm$^2$) would result in an adsorbed mass of 0.058 and 0.145 μg/cm$^2$, respectively. Thus the patterns shown in FIG. 6 are consistent with multi-layer adsorption in each case. Nisin adsorption to the F108-coated surface was generally slower than adsorption to the bare hydrophobic surface, likely owing to steric inhibition by the pendant PEO chains. Nisin elution in protein-free buffer was similar at each surface initially, but elution was observed to continue only at the bare hydrophobic surface. Presumably, this is due to greater solvent accessibility to nisin that is loosely held in the outer layers in the case of adsorption to the uncoated surface, while nisin integrated into the PEO "brush" would show greater resistance to elution.

Example 5

Nisin Adsorption and Elution on Pluronic® F108 (Covalent or Non-Covalent Attachement) Coated on the Surface of Silanized Glass PLURONIC® F108 triblocks were coated as hydrophobic association with the silica surfaces and on a different set of silica surfaces F108 triblocks were coated by covalent attachment via the PPO chains. For this purpose, the silica samples were silanized with octadecyltrimethoxysilane, the surface-polymer covalent attachment induced by UV radiation. Ellipsometry was performed as described in Example 4 to obtain adsorption and elution kinetics of nisin at hydrophobic surfaces coated with F108 by hydrophobic association, and by covalent attachment.

Figure 7:
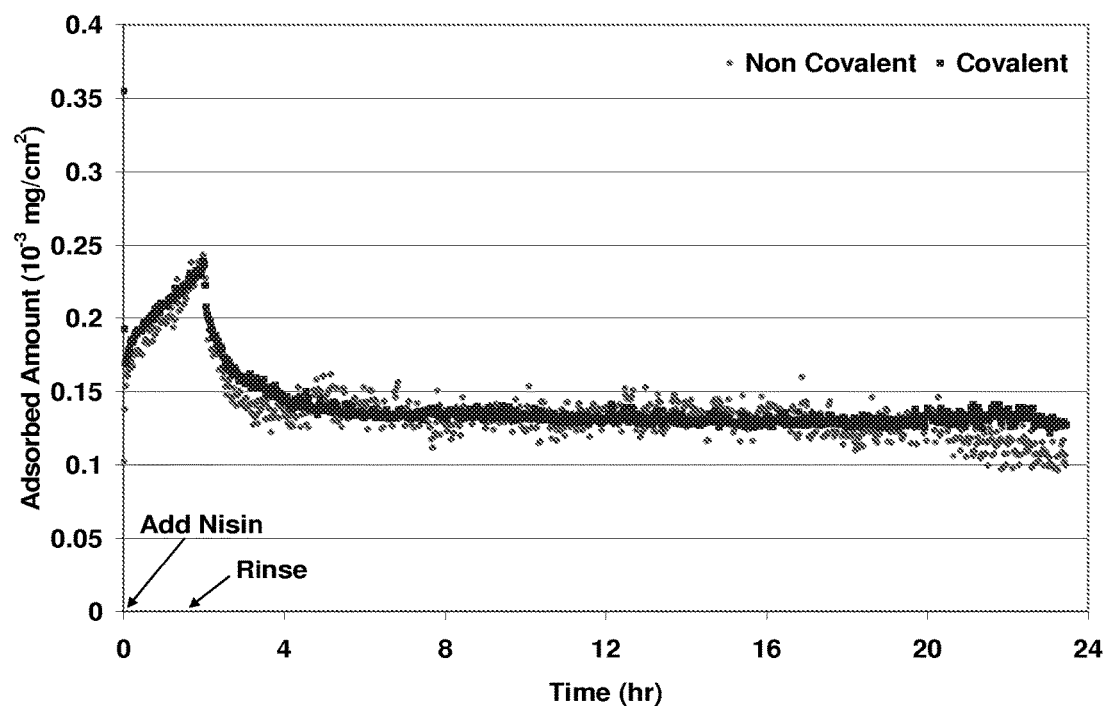
FIG. 7 contains experimental results depicting nisin adsorption and elution kinetics recorded at hydrophobic surfaces that have been coated with F108 by hydrophobic association, and by covalent attachment.

As shown in FIG. 7, the nisin adsorption and elution kinetics were quite similar at each surface, indicating that the F108 layers prepared by hydrophobic association between the PPO block and the silanized surface functioned in a manner substantially similar to the F108 layers prepared by covalent attachment between the PPO block and silanized surface.

Example 6

Preparation of Thiolated Nisin Using SATA and Measurement of Activity

Preparation of Thiolated Nisin Using SATA:

N-Succinimidyl-5-acetylthioacetate (SATA) (Pierce Biotechnology, Rockford, Ill.) was used to incorporate a protected thiol at the n-terminus of nisin. A typical thiolation proceeds as follows. A nisin solution containing 10 mg/mL in trifluoroacetic acid (TFA) is prepared. The pH of the nisin solution is raised by adding monobasic and dibasic potassium buffers containing ethylenediaminetetraacetic acid (EDTA) to obtain a final composition of 0.5 mg/mL nisin in 20 mM potassium phosphate buffer at pH 7.0, 10 mM EDTA. Immediately prior to reaction, SATA is dissolved in dimethyl sulfoxide (DMSO) at a desired concentration, such as 20 mM. An aliquot of the SATA solution is mixed with the nisin solution to obtain a desired molar excess of SATA to nisin. In this example, the molar excess of SATA to nisin was varied between 2.5:1 to 5:1. The reaction mixture is wrapped in aluminum foil to exclude light and the reaction is allowed to proceed for 30 minutes at room temperature. After which, excess SATA is removed by dialysis or by passing the reaction mixture through a desalting or gel filtration column. Generally, a column packed with SEPHADEX G-10 (MWCO 800 Da) is used with the eluant being 20 mM potassium phosphate buffer. The fractions containing nisin are collected and pooled. The modified nisin is then deacetylated by adding a solution of hydroxylamine-HCl (0.5 M Hydroxylamine-HCL (Pierce Biotechnology), 25 mM EDTA, in phosphate buffer, pH 7.8). The deacetylation reaction is allowed to proceed for two hours at room temperature. The thiolated nisin is then recovered by passing the reaction mixture through a column packed with SEPHADEX G-10 and eluting the thiolated nisin with 20 mM potassium phosphate buffer. The degree of nisin derivatization with SATA was determined using the Ellman's Assay [16].

The thiolation reaction with SATA, or other crosslinkers containing an N-hydroxysuccinimide (NHS) ester, will proceed with any sufficiently available, primary amines on the protein. In the case of nisin (see structure in FIG. 1 above), reaction is possible at the N terminal amine, Lys 12, Lys 22, and the C-terminal residue, Lys 34. It is believed that thiolation and eventual linkage to PEO via residue 12 or 22 will result in inactive forms of nisin. Structural analysis shows Lys 34 (as well as Ile 1) to be more solvent accessible and mobile than residues 12 and 22. In this regard, if lysines were allowed to undergo thiolation we would expect preferential thiolation of the end residue over the interior residues. If tethered via Lys 34, with reference to the barrel-stave model of pore formation one would expect an inactive form, as penetration of the C-terminal domain into and through the lipid bilayer will be compromised. With reference to the wedge model one might expect some activity as the hydrophilic PEO chain would not have to be "dragged" through the hydrophobic core of the bilayer. In any event, preferential thiolation of the N-terminal residue is accomplished by taking advantage of the differences in pKa of the N-terminal amine, and the amine on lysine. The N-terminal amine typically has a pKa between 6.8 and 8, while the pKa of the amino group on lysine is about 11.1. At neutral pH, most of the lysines would be in their ionized form and therefore not reactive. As the pH is increased, the lysines will become increasingly reactive and hydrolysis of the SATA reagent will occur more rapidly. In this regard, selecting a lower reaction pH, time, and/or concentration will ensure that the majority of reactions occur at the N-terminal domain.

The thiolated nisin as well as several control samples were tested for activity. Controls included nisin samples that were withdrawn at the end of each treatment step [viz. (i) 30 min incubation following SATA/DMSO addition; (ii) gel filtration; (iii) hydroxylamine-HCl/pH7.8 addition followed by 2 hours incubation and (iv) gel filtration) and diluted by pH 7.0 phosphate buffer to the peptide concentrations expected in the final gel filtration column effluent] as well as nisin samples that were exposed to the reaction conditions described above but in the absence of SATA.

Figure 8:
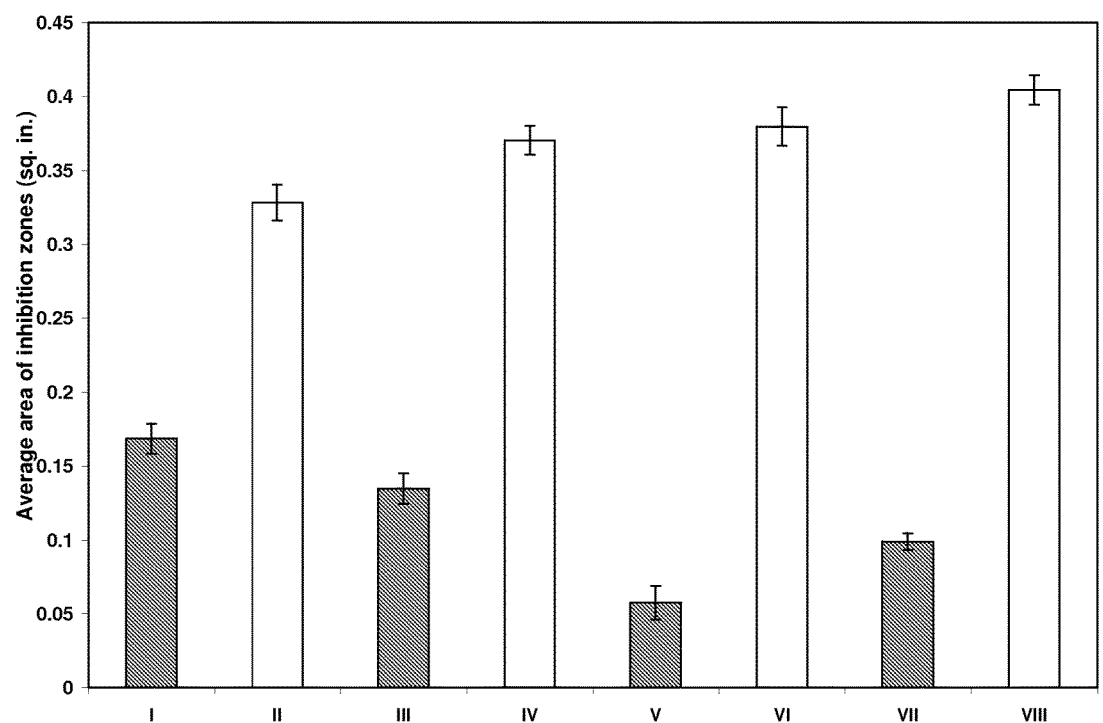
FIG. 8 contains experimental results depicting the antibacterial activity of nisin at various stages of SATA crosslinking.

Measurement of Activity of Thiolated Nisin:

Antibacterial activity of modified nisin was determined by the agar well diffusion assay, using the Gram positive bacterium *Pediococcus pentosaceus* FBB 61-2 (ATCC, Manassas, Va.) as the indicator strain. Ten milliliters of a 52.2 g/l solution of deMan-Rogosa-Sharpe broth, MRS (EMD Chemicals, Germany) was sterilized by autoclaving according to manufacturer's instructions. *P. pentosaceus* culture stock was thawed and 10 μl was added to the autoclaved MRS broth using a sterile inoculation loop. The inoculated broth was then incubated overnight at 37° C. resulting in a cell count of about $10^7$ CFU/ml. Powdered agar (Becton-Dickinson, Sparks, Md., USA) was dispersed in 52.2 g/l MRS broth and liquefied by autoclaving. This was cooled to 40° C. and seeded with the *Pediococcus* overnight culture prepared as above, and poured in several Petri dishes (100 mm dia.×15 mm depth) to a depth of about 5 mm and allowed to solidify. Three holes were drilled aseptically in each agar plate using a cork borer and 10 μl of thiolated nisin solution or control solution was added per well. In all cases, the solutions were diluted with phosphate buffer to provide an approximately equal concentration of nisin in each solution being tested. The plates were covered and incubated for 24 h at 37° C. and the diameters of the inhibition zones around each well were measured. The results are shown in FIG. 8. Specifically, FIG. 8 illustrates the effect of SATA crosslinking on nisin antibacterial activity, compared to "control nisin" to which only DMSO was added. In FIG. 8, (I) refers to nisin+SATA in DMSO (30 min reaction); (II) refers to nisin+DMSO (30 min: control); (III) refers to nisin+SATA through a SEPHADEX column for SATA removal; (IV) refers to nisin+DMSO through a SEPHADEX column; (V) refers to nisin-SATA+hydroxylamine-HCl (2 hr reaction); (VI) refers to nisin+buffer (2 h reaction, control); (VII) refers to nisin-SH through a SEPHADEX column for hydroxylamine-HCl removal; and (VIII) refers to nisin+DMSO through a SEPHADEX column. It can be seen from FIG. 8 that it was possible to retain some nisin activity after treatment with SATA. Maximum activity loss was observed after the deacylation step, however this was found to be partly reversible upon removal of hydroxylamine-HCl.

Example 7

Preparation of Thiolated Nisin Using SAT(PEO$_4$) and Measurement of Activity

N-Succinimidyl S-acetyl(thiotetraethylene glycol) Ester (SAT(PEO$_4$)) (Pierce Biotechnology, Rockford, Ill.) was used to incorporate a protected thiol at the n-terminus of nisin. A nisin solution containing 10 mg/mL in trifluoroacetic acid (TFA) is prepared. The pH of the nisin solution is raised by adding monobasic and dibasic potassium buffers containing ethylenediaminetetraacetic acid (EDTA) to obtain a final composition of 2.0 mg/mL nisin in 20 mM potassium phosphate buffer at pH 7.0, 1 mM EDTA. Immediately prior to reaction, SAT-PEO is dissolved in dimethyl sulfoxide (DMSO) to obtain a 250 Mm stock solution. An aliquot of the SAT-PEO solution is mixed with the nisin solution to obtain a desired molar excess of SAT-PEO to nisin. In this example, the molar excess of SAT-PEO to nisin was varied between 1.085 and 4.34. The reaction mixture is wrapped in aluminum foil to exclude light and the reaction is allowed to proceed for 30 minutes at room temperature on a rotary shaker. After completion of the reaction, excess SAT-PEO is removed by passing the reaction mixture through a gel filtration column packed with SEPHADEX G-10 (MWCO 800 Da) and eluted with 20 mM potassium phosphate buffer. The fractions containing nisin are collected and pooled. The modified nisin is then deacetylated by adding a solution of hydroxylamine-HCl (0.5 M Hydroxylamine-HCL (Pierce Biotechnology), 25 mM EDTA, in phosphate buffer, pH 7.8). The deacetylation reaction is allowed to proceed for two hours at room temperature. The thiolated nisin is then recovered by passing the reaction mixture through a column packed with SEPHADEX G-10 and eluting the thiolated nisin with 20 mM potassium phosphate buffer. The degree of nisin derivatization with SAT-PEO was determined using the Ellman's Assay [16].

Measurement of Activity of Thiolated Nisin:

The activity of nisin thiolated using SAT-PEO was measured using the agar well diffusion assay as described above in Example 7. A summary of the results for three trials of nisin block copolymers prepared using 1.085 fold molar excess of SAT-PEO, are shown below in Table 1 and illustrate that the peptide could be derivatized to incorporate thiol groups while maintaining reasonable levels of antibacterial activity.

TABLE 1

| % Thiol groups on nisin | Inhibition zone diameter (mm ± SD) | $\Delta OD_{343}$ for block co-polymer | Peptide content (μg/mL) of EGAP-nisin construct | | | |
|---|---|---|---|---|---|---|
| | | | $OD_{343}$ | | BCA assay | |
| | | | EGAP | F108 | EGAP | F108 |
| 40.56 | 19.06 ± 0.18 | 0.129 | 56.18 | N/A | Not determined | Not determined |
| 48.44 | 18.5 ± 0.15 | 0.191 | 83.18 | N/A | 110.207 | 37.95 |
| 56.04 | 17.3 ± 0.40 | 0.22 | 95.81 | N/A | 100.268 | 65.36 |

Example 8

Nisin Coupling to End-Group Activated PEO-PPO-PEO Triblocks (Copolymers) and Measurement of Activity Nisin Coupling to End-Group Activated PEO-PPO-PEO Triblocks (Copolymers):

PLURONIC® F108 (BASF) is derivatized to incorporate a terminal pyridyl disulfide group according to the procedure of Li et al [15]. The end group activated copolymer (EGAP-PDS) is routinely produced having a degree of substitution between 1 and 1.2 pyridyl disulfide ("PDS") groups per F108 molecule. F108 is an appropriate starting material because its (fully extended) PEO chains are about 60 nm long. Nisin must pass through the cell wall of susceptible Gram positive bacteria in order to interact with the membrane. Cell wall thicknesses vary among bacterial species, but on average, the susceptible Staphylococcal cell wall is 20 to 30 nm thick.

Three hundred microliters of the thiolated nisin solution is added to microcentrifuge tubes containing 100 μl of either EGAP-PDS or F108 dissolved in potassium phosphate buffer, pH 7.0. Final concentrations in either case ranged from 0.2-fold to five-fold molar excess of triblock copolymer over the modified peptide. The tubes are wrapped with aluminum foil and incubated overnight at room temperature with continuous mixing. Unreacted nisin is removed by dialysis against phosphate buffer, pH 7 using a Slide-A-Lyzer® cassette (Pierce Biotechnology) with a MWCO of 10,000 Daltons according to the manufacturer's instructions. The extent of coupling between nisin and EGAP-PDS is determined by measuring the concentration of PDS groups released during the reaction. This is accomplished by measuring the absorbance at 343 nm of the reaction mixture at time zero ($t_0$) and at the completion of the reaction prior to dialysis ($t_f$). The difference between the Absorbance at $t_0$ and $t_f$ is then used to calculate the concentration of PDS groups using an extinction coefficient of 8060 $M^{-1}$.

Additional controls to those mentioned above, included 100 μl solutions of each type of triblock (end-activated and otherwise) to which 300 μl phosphate buffer was added in place of thiolated nisin solution. These were prepared to see the effect of the triblocks themselves on bacterial growth.

Figure 9:
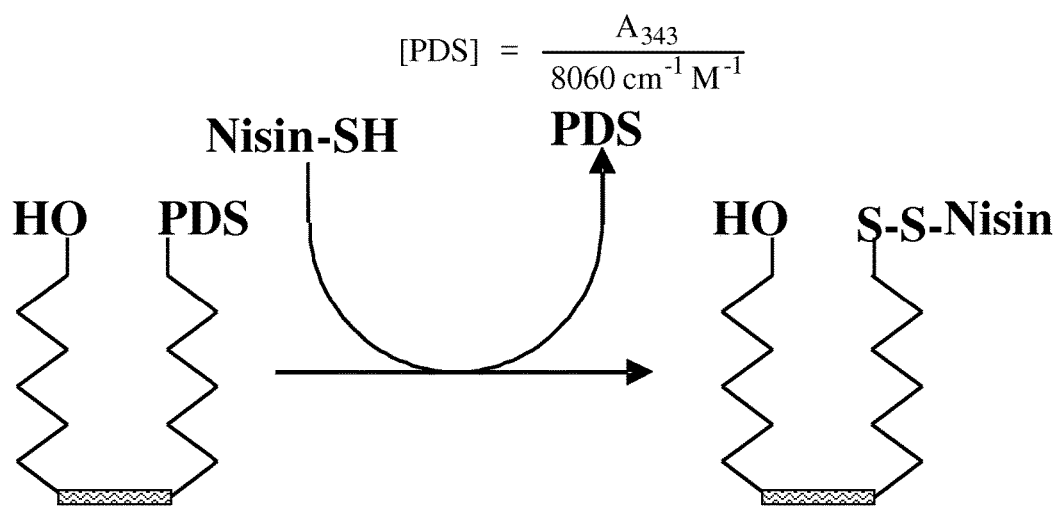
FIG. 9 illustrates a representative manner for linking nisin to a block copolymer.

FIG. 9 demonstrates the linking of the nisin to the block copolymer, as taught herein.

Measurement of Activity of Copolymer-Nisin Constructs:

The identification of lipid II in bacteria as a specific target for nisin, as explained above, has enabled a clearer picture of structural and functional relationships in nisin to emerge. Nisin has been shown to kill bacteria via three different mechanisms. In order of potency, they are: (i) binding to lipid II and subsequent pore formation; (ii) binding to lipid II in the absence of pore formation, and (iii) target-independent pore formation, in the absence of lipid II. For each mechanism, specific structural and functional features of the peptide have been identified. The combination of killing mechanisms (i) and (ii) in one molecule potentiates antimicrobial activity and results in minimal inhibitory concentrations in the nanomolar range.

Although not being limited by this theory, it is believed that the present compounds and methods involve securing nisin to flexible, PEO chains in an "end-on" orientation, through a linkage with the primary amine of the N-terminal isoleucine. (See FIG. 1 for a structure of nisin.) In this way, N-terminal domain binding to lipid II should be unaffected, as should the flexibility of the hinge region.

Figure 10:
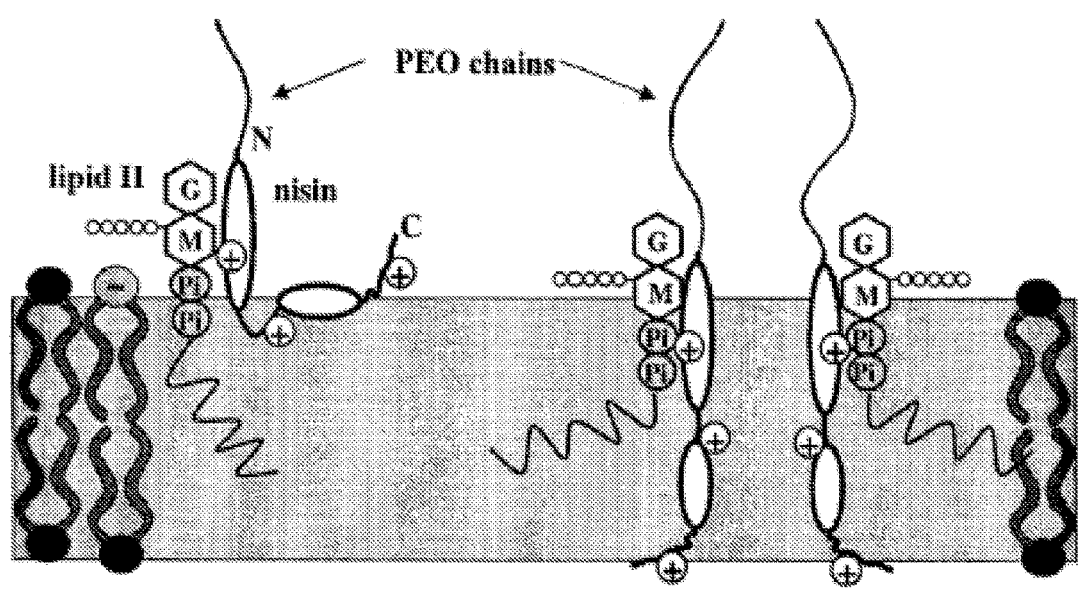
FIG. 10 contains a illustration of a proposed model for lipid II-mediated pore formation by tethered nisin.

A schematic of lipid II-mediated pore formation by nisin tethered in this way is proposed in FIG. 10. Specifically, in FIG. 10 the orientation of nisin relative to the membrane and relative to lipid II, for both lipid II binding (left) and pore formation (right), is as depicted by Wiedemann et al. [17] and van Heusdan [18]. In FIG. 10, nisin first binds to the carbohydrate moiety of lipid II via its N-terminal domain. The C-terminal part of nisin is then assumed to translocate to some extent across the membrane. For this step the flexible hinge region between ring clusters is important. In FIG. 10, N-acetylated sugars GlcNAc and MurNAc are shown as hexagons labeled G and M, respectively. The amino acids of the pentapeptide attached to the MurNAc are shown as five circles. The circles labeled Pi identify the pyrophosphate moiety in lipid II which links the sugar-peptide group to the hydrophobic tail. Nisin is represented in FIG. 10 by its functionally important domains: the large oval represents the N-terminal domain and the small oval represents the C-terminal domain. The domains are connected by the short hinge region. The short linear peptide sequences preceding ring A (N-terminal, labeled N) and following ring E (C-terminal, labeled C) are shown in FIG. 10 as well.

Several nisin-lipid II complexes are presumed to assemble for a functional pore thus explaining the rapid efflux from liposomes and living cells of molecules of the size of carboxyfluorescein, amino acids, and ATP, but the exact number is not currently known. In any event the concentration of tethered nisin in the environment of the interface will be high. Thus it is believed that the films will demonstrate a high level of activity, and at the same time overcome limitations associated with film formation/loading by direct adsorption.

The activity of copolymer-nisin constructs was tested using the bacterial culture suspension assay instead of the agar well diffusion assay because the size and structure of the constructs would hinder their diffusivity in the solid agar medium relative to control nisin. Disulfide exchange reactions would be expected to occur slowly, over time in the body. This may lead to some prolonged release of nisin from EGAP. Given this potential mechanism of release, copolymer nisin constructs were also tested for activity after reduction by DTT.

Figure 11:
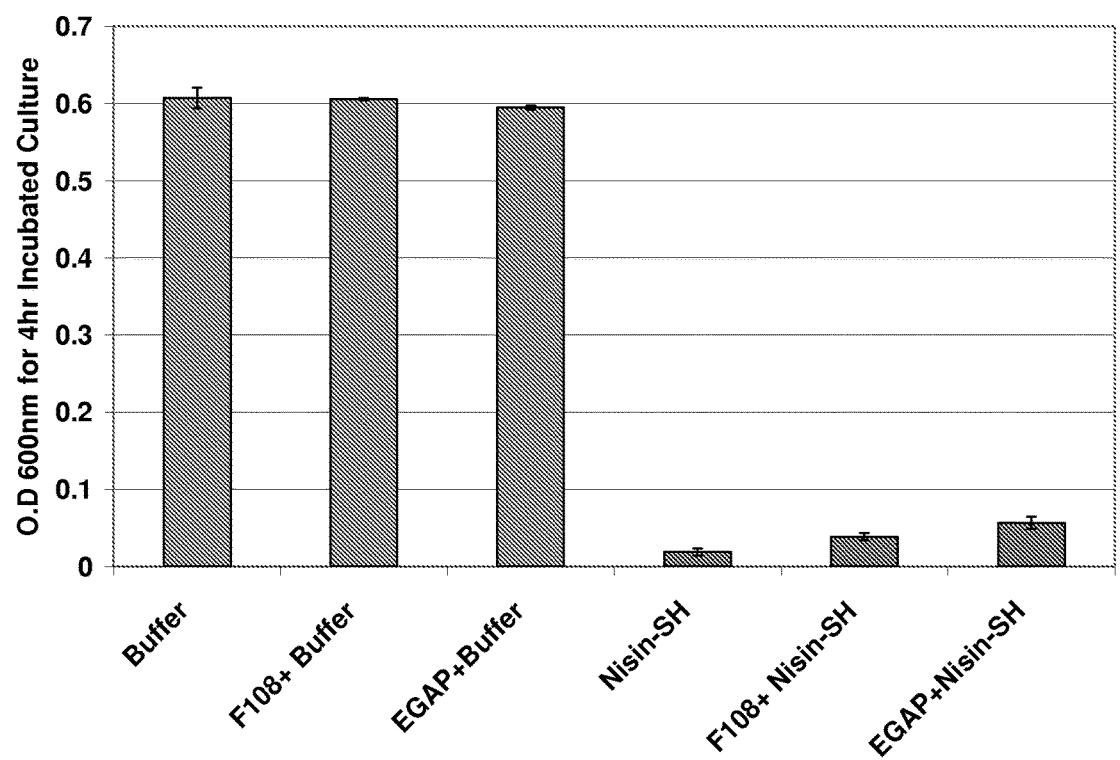
FIG. 11 contains experimental results showing the antibacterial activity of EGAP-nisin copolymers and controls.
Figure 12:
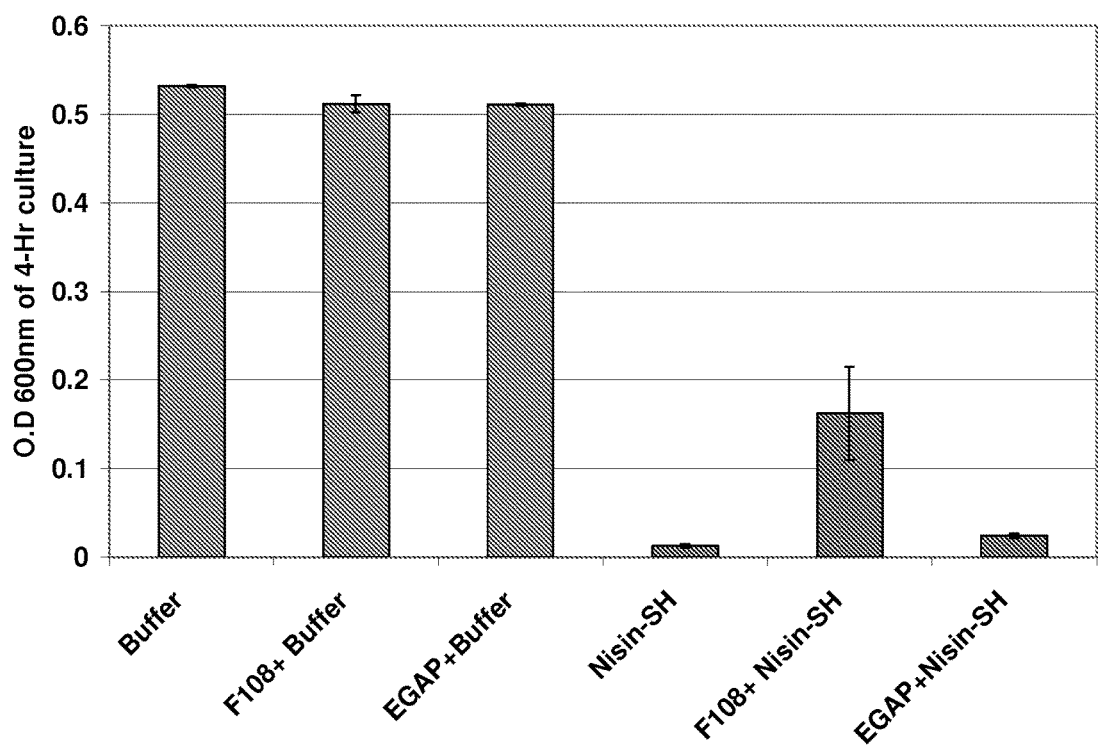
FIG. 12 contains experimental results showing the antibacterial activity of nisin containing block polymers and controls after DTT treatment.

Overnight cultures of *Pediococcus* were prepared as described in Example 6 and diluted 100-fold in sterile MRS broth to give a cell count of about $9 \times 10^5$ CFU/ml. Nine hundred microliters of this dilute culture were transferred to a 15 ml polypropylene tube. One hundred microliters of a copolymer (end-activated or otherwise) solution, that had either been reacted with thiolated nisin or combined with phosphate buffer, was then added to this tube and all such tubes were incubated at 37° C. for 4 h with constant agitation. The thiolated nisin solution as well as copolymer-free, nisin-free phosphate buffer were also tested in this manner. At the end of the incubation period, the cell density of each culture was determined at 600 nm. Results are shown in FIG. 11 for EGAP-nisin constructs prepared using nisin that was thiolated with SAT(PEO$_4$). Specifically, FIG. 11 shows results for the antibacterial activity of EGAP-nisin copolymers and controls. In particular, FIG. 12 shows results for the antibacterial activity of nisin containing block copolymers and controls after DTT treatment. For both FIGS. 11 and 12, a molar excess of SAT(PEO$_4$) of 1.085 was used for the nisin thiolation reaction and a molar excess of EGAP to nisin-SH of 5 was used for preparation of the constructs.

Alternative linking strategies, possibly involving protein engineering techniques, could be used to prepare tethered lantibiotics. For example, thoughtful incorporation of a cysteine residue in the molecule would preclude the need for chemical modification preceding linkage to PEO using the EGAP-PDS described here. This may be problematic because cysteine residues in the precursor peptides of lantibiotics supply the thiol groups involved in forming the thioether linkages during post-translational modification, but it is just one among many solutions presented by protein engineering. Protein engineering with lantibiotics is still less straightforward than for enzymes and structural proteins, as expression systems must include not only the structural genes but also the genes encoding biosynthetic enzymes, immunity protein and regulatory proteins [80]. In addition, proper post-translational modification of specific residues is in many cases required for production and secretion of lantibiotics with any activity. Nevertheless, a number of site-directed nisin mutants have been prepared with similar, reduced, and even increased activity in relation to the wild type, and such an approach may eventually contribute to rational design of lantibiotics optimally suited for application at interfaces.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

Example 9

Nisin and Nisin in Combination with Copolymers Coated on Medical Grade Polyurethane and Measurement of Activity Medical device grade PU tubing, 80 Shore A, (Scientific Commodities Inc., Lake Havasu City, Ariz.) was cut into 1 cm lengths, washed with 99% isopropanol for 30 min, and then rinsed once with sterile, DI water for 5 min. Samples were incubated overnight with either water, 1% F108 or 1% EGAP-NTA that had been sterile filtered. The samples to be further treated with nisin were then rinsed 3 times with phosphate buffer, pH 6.0. The remaining samples were rinsed 3 times with PBS (20 mM PB, 150 mM NaCl, pH 7.4). A nisin solution (0.5 mg/mL in 0.01M PB, pH 6.0) was added to the appropriate samples and incubated overnight. These samples were then rinsed 3 times with PBS.

A Standard Bacteria Solution as indicated in Example 1 was prepared and was added to the samples in 1.5 mL polystyrene tubes. The bacteria cultures were incubated with samples for 24 hours at 37° C. The samples were washed 3 times with PBS and then placed in new sterile 1.5 mL polystyrene tubes. MRS broth was added and the samples were sonicated for 5 min. Post sonication, a 100 µl aliquot of each sample diluted 1:10 and 1:100 was streaked on individual agar plates. The number of colonies formed on each agar plate was counted after a 48 h growth period.

Figure 13A:
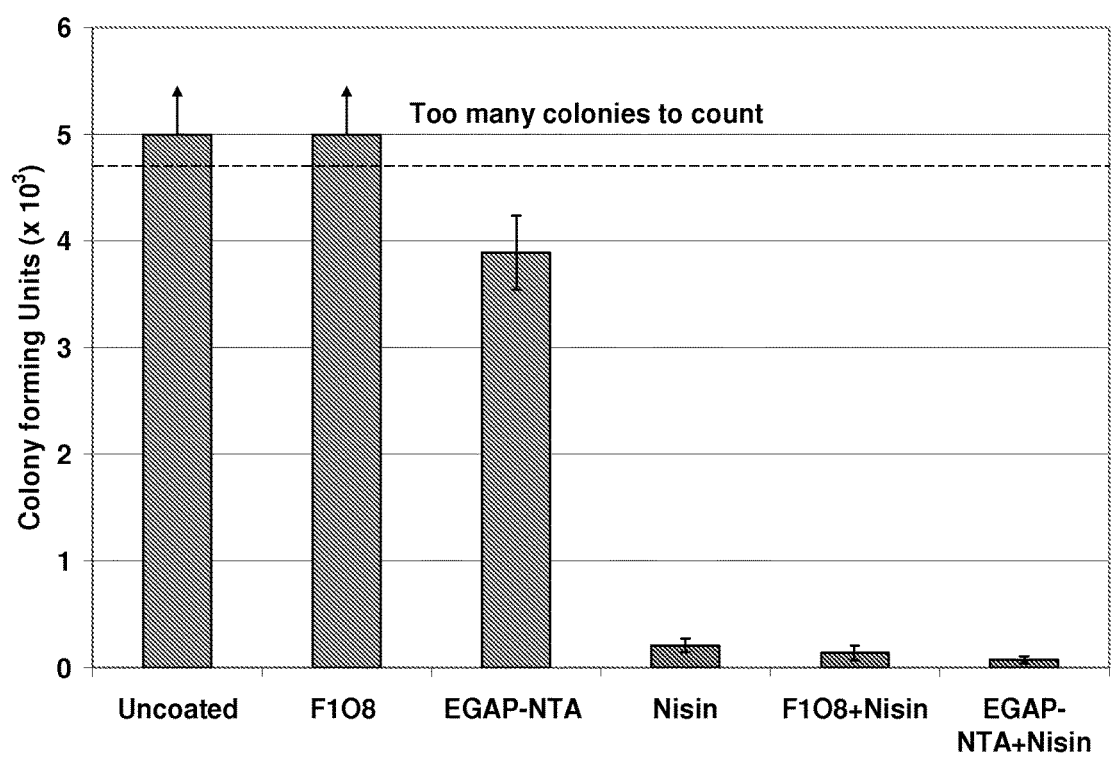
FIG. 13A contains experimental results showing bacteria adhesion on coated and uncoated PU tubing at 24 hours in the presence of MRS broth.
Figure 13B:
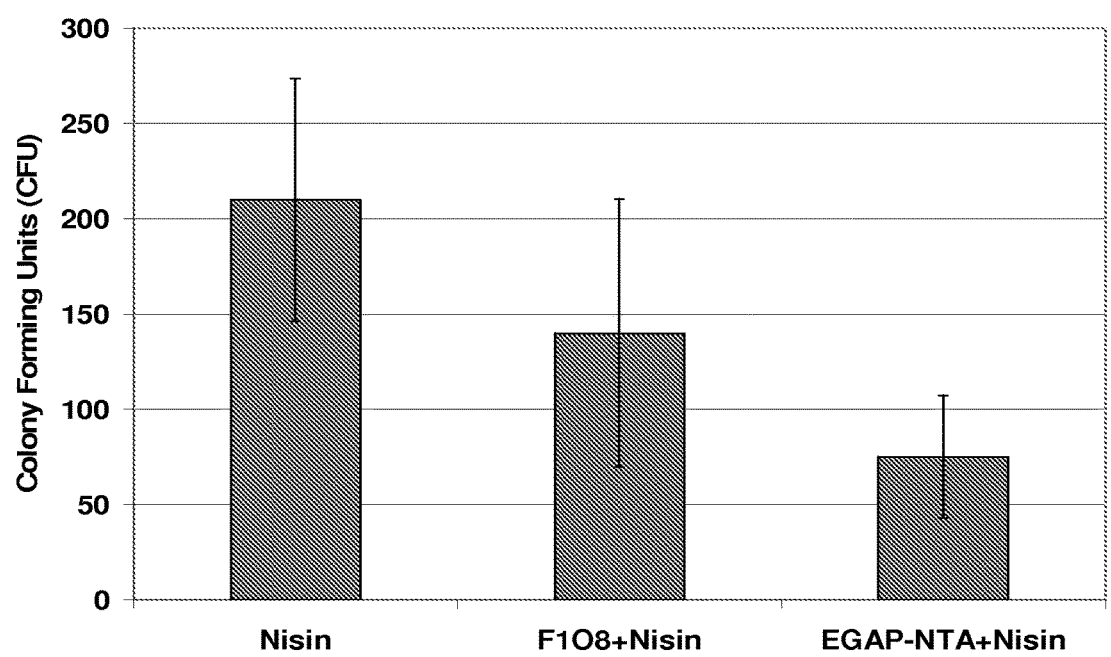
FIG. 13B contains experimental results showing a comparison between bacteria adhesion on nisin coated and nisin in combination with copolymers on polyurethane surface.
Figure 14:
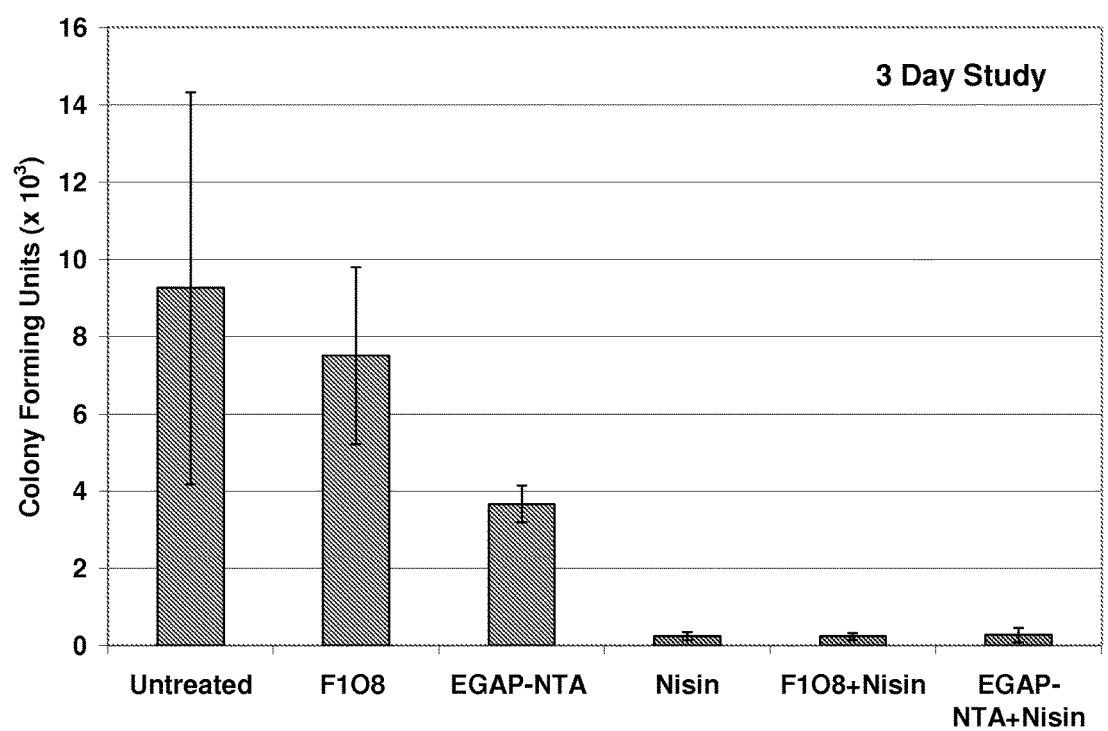
FIG. 14 contains experimental results showing bacteria adhesion on polyurethane tubing at 3 days in the presence of MRS broth.

Results:

FIG. 13A shows a substantial inhibition of bacteria on all surfaces coated with nisin and a trend toward increasing effectiveness when nisin is coated with F108 and further with EGAP-NTA as shown in FIG. 13B. Specifically, FIG. 13a illustrates the results for Bacteria adhesion on coated and uncoated PU tubing at 24 hours in the presence of MRS broth. FIG. 13B illustrates a comparison between bacteria adhesion on nisin coated and nisin in combination with copolymers on a polyurethane surface. Similarly encouraging results regarding bacteria adhesion were obtained with PU tubing after 3 days in the presence of MRS broth (FIG. 14).

Example 10

Nisin Stability and Activity on the Surface of Polyurethane Catheters in the Presence of Blood Proteins Polyurethane catheter segments (22 GA, 1.0 in I.V. catheters, REF 381423, Becton Dickinson) were coated by incubation with F108 (5 mg/mL) in 10 mM phosphate buffer for 24 h in disposable test tubes. They were then rinsed with multiple test tube volumes of phosphate buffer to remove unbound F108.

F108-coated and bare segments were incubated in 0.5 mg/mL nisin for 1 h at room temperature. After 1 h, the catheter segments were rinsed with multiple test tube volumes of filtered 10 mM sodium phosphate buffer to remove unbound nisin. Nisin treated catheter segments were then incubated in 25% equine serum or 10 mM phosphate buffer for a desired period of time. The nisin-treated segments were then rinsed with copious phosphate buffer, in each case administered to the lumen through a syringe.

Nisin sensitive *P. pentosaceus* (cultivated as outlined in Example 3) were used to seed MRS agar dishes. Rinsed catheter segments were inserted onto the *P. pentosaceus*-seeded plates for an agar diffusion assay of antibacterial activity. Plates were incubated at 37° C. for 48 h, and the area of the kill zone was measured to provide an indication of nisin activity.

Figure 15:
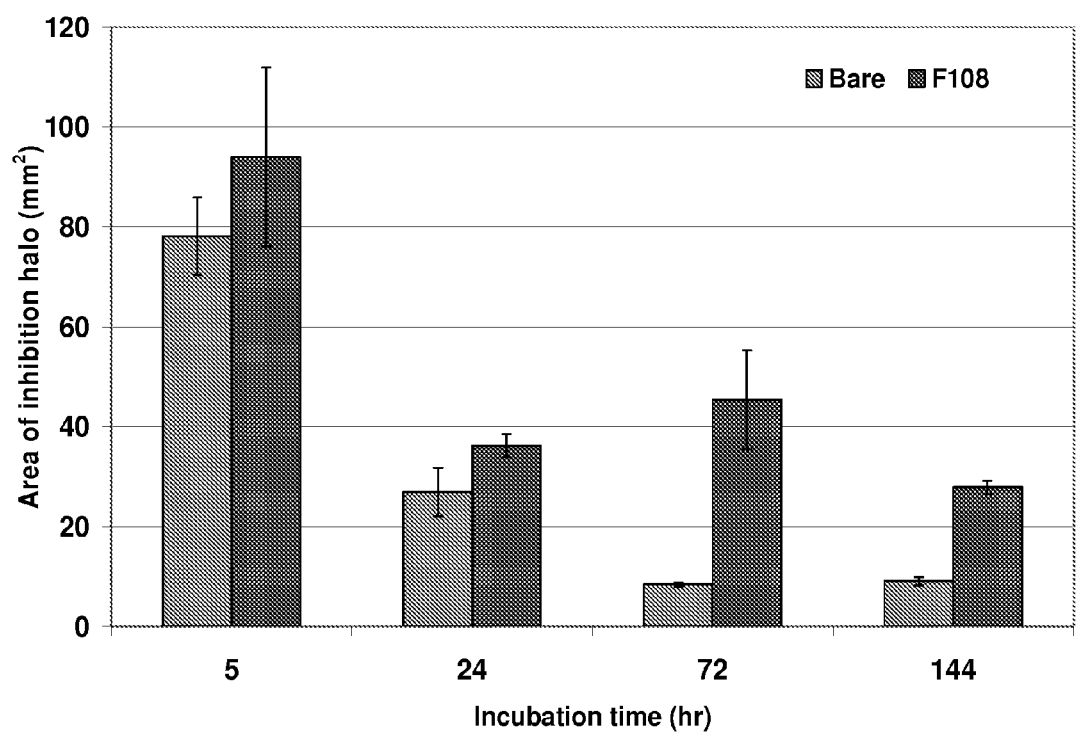
FIG. 15 contains experimental results showing antimicrobial activity retained by catheter segments after contact with nisin and incubation in 25% horse serum.

The results are shown in FIG. 15. When the catheter segments were challenged by blood proteins (25% horse serum), a larger contrast is observed between the F108-coated and bare surface groups, especially with increasing incubation time. These results support the notion that the pendant PEO chains of the F108 coating inhibited the exchange of nisin by blood proteins.

Example 11

Stabilizing Pluronic® F108ON Polyurethane Surface Using Irradiation

Figure 16:
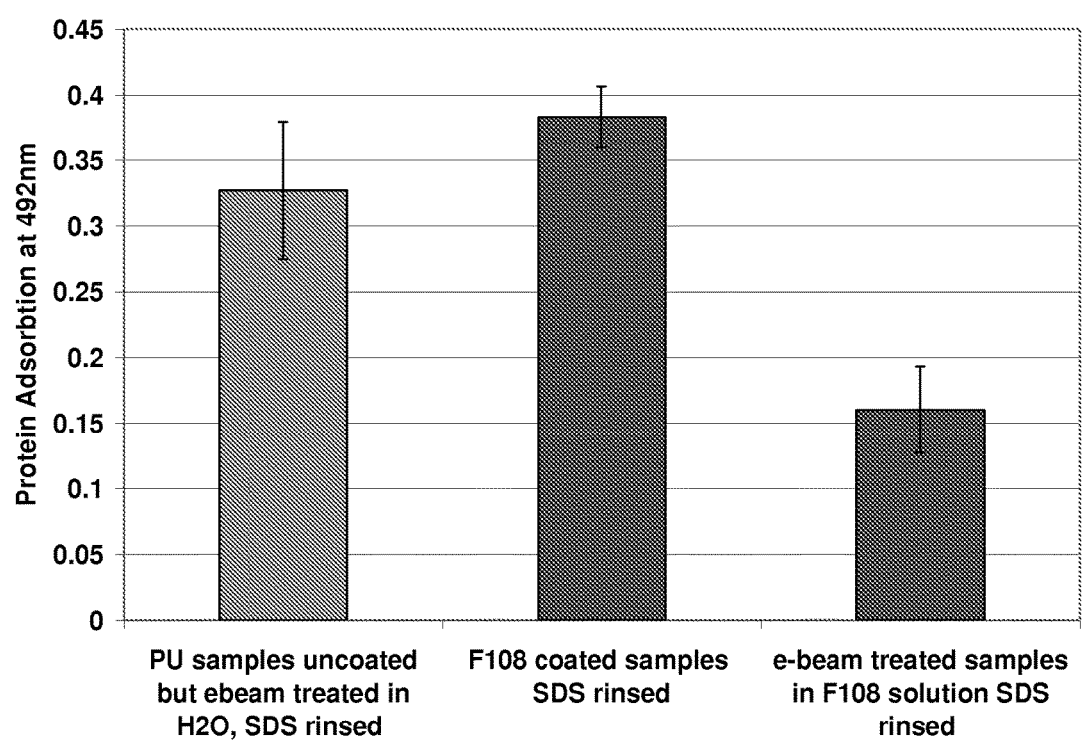
FIG. 16 contains experimental results showing the effect of irradiation on the stabilization of a PLURONIC® F108 coating.

Two types of irradiation were evaluated, e-beam and UV. Durability was evaluated by thoroughly washing with an SDS solution and then conducting a protein adsorption assay, where retention of the copolymer is evidenced by reduced protein adsorption. FIG. 16 contains results showing the effect of irradiation on the stabilization of PLURONIC® F108 coating. The results shown in FIG. 16 indicate it is feasible to stabilize unmodified copolymers or EGAP on PU by application of irradiation under certain conditions.

Example 12

The Effect of PEO Chains in the Adsorption and Elution of Nisin

The effect of the PEO chains in adsorption and elution can be further revealed by analysis of nisin adsorption-elution data with reference to a "history dependent" adsorption mechanism [21, 22]. A number of macromolecular species, including proteins, exhibit history dependent adsorption behavior owing to the slow relaxation of non-equilibrium structures at the interface. That is, for a given protein at a given surface loading, the rate of adsorption depends on the formation history of the adsorbed layer. This is particularly relevant near monolayer surface coverage when protein-protein interactions can influence the availability of surface area suitable for adsorption. Tie et al [22] studied the adsorption of fibronectin, cytochrome c and lysozyme using optical waveguide lightmode spectroscopy in multi-step mode, where an adsorbing surface is alternately exposed to a protein solution and a solution free of protein. In general, they observed the initial adsorption rate during the second step exceeded that observed at the same surface coverage during the first step. They postulated that, for a given mass density at an interface, if proteins were arranged in "clusters" or aggregates, more "cleared" surface area would be available for further adsorption relative to proteins being randomly distributed. On the other hand, if the adsorbed protein films were at equilibrium, we would expect the same adsorption rates during each cycle, since the proteins would have identical structural characteristics.

Figure 17:
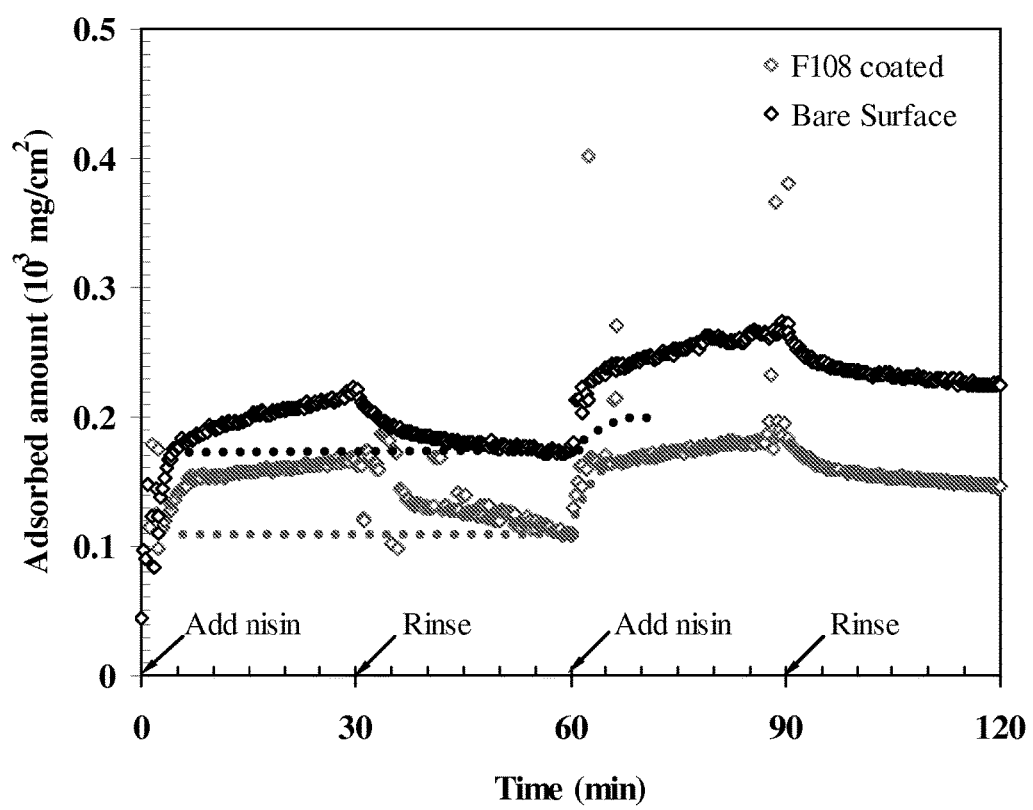
FIG. 17 contains experimental results showing sequential adsorption and elution kinetics exhibited by nisin at bare hydrophobic and PLURONIC® F108-coated surfaces. Data recorded during the first adsorption cycle are overlaid on the second adsorption cycle in order to compare adsorption rates recorded at the same initial mass density, but after different formation histories.

Adsorption rate data can thus provide important information relevant to adsorbed layer structure [21, 22], and we used the kind of sequential adsorption kinetic data presented in FIG. 17 for this purpose. FIG. 17 shows results of a two, nisin adsorption-elution steps performed in sequence at a bare hydrophobic surface and an F108-coated surface. For each surface, the initial slope of the second adsorption step was compared to the slope at the point in the first adsorption cycle with the same initial mass density. At both the coated and uncoated surface, the initial adsorption rate during the second step exceeded that observed at the same surface coverage during the first step. But the increase in slope was substantial in the case of uncoated silica as compared to F108-coated silica. That is, the first and second step adsorption rates were not as different for the F108-coated surface, indicating that less post-adsorptive rearrangement (or less "clustering") of nisin occurred in this case. We suggest the lateral mobility needed for cluster formation and the generation of unoccupied surface area was inhibited by the PEO chains.

Comparison of nisin adsorption and elution kinetics at uncoated and F108-coated surfaces (FIGS. 6, 7, & 17) suggested that the rate of nisin adsorption and elution, and its lateral mobility at the interface, were generally greater at uncoated surfaces. This would be consistent with nisin adsorption or "entrapment" within the PEO brush layer, as opposed to adsorption to the PEO chains in a non-penetrating manner.

Example 13

The Effect of PEO Chains on Nisin Structural Characteristics

Silica nanoparticles, made hydrophobic by silanization with hexamethyldisilazane (Product R816, 190 m$^2$/g, 10-12 nm diameter, Degussa), were coated with F108 by suspension in phosphate buffer overnight on a rotator. The amount of F108 used for this purpose (1.35 mg/mL) was selected as sufficient to cover the surface area presented by the nanoparticles in suspension, based on a specific coating density of F108 estimated to be 3.3 mg/m$^2$ [5]. F108-coated and bare hydrophobic silica nanoparticles were then incubated with nisin (0.5 mg/mL) for a desired period of time (4 h to 1 week) at room temperature. The amount of nanoparticles selected for combination with nisin (2.19 mg/mL nanoparticles) provided 1.25 times more surface area than that required to support a nisin coating of 0.15 µg/cm$^2$. Nisin adsorption was allowed to occur for 2 h. A nisin loading of 0.15 µg/cm$^2$ is consistent with monolayer adsorption (based on dimensions of nisin in solution, a monolayer of molecules adsorbed "end-on" would result in an adsorbed mass of about 0.145 µg/cm$^2$), and earlier work with in situ ellipsometry indicated that 2 h would provide abundant time for adsorption to that level.

CD spectra of nisin-nanoparticle suspensions and control samples were recorded between 300 and 180 nm on a Jasco J-720 spectropolarimeter with a 0.2 mm path length and cylindrical cuvette at 25° C. In each case six scans were recorded and averaged in order to increase the signal-to-noise ratio. CD spectra of nisin-loaded nanoparticle suspensions and controls were recorded along with reference samples in each case (nanoparticles+buffer, nanoparticles+F108+buffer, F108+buffer, and buffer only) in order to subtract background signals and ensure the measurement of nisin structural properties only.

Figure 18:
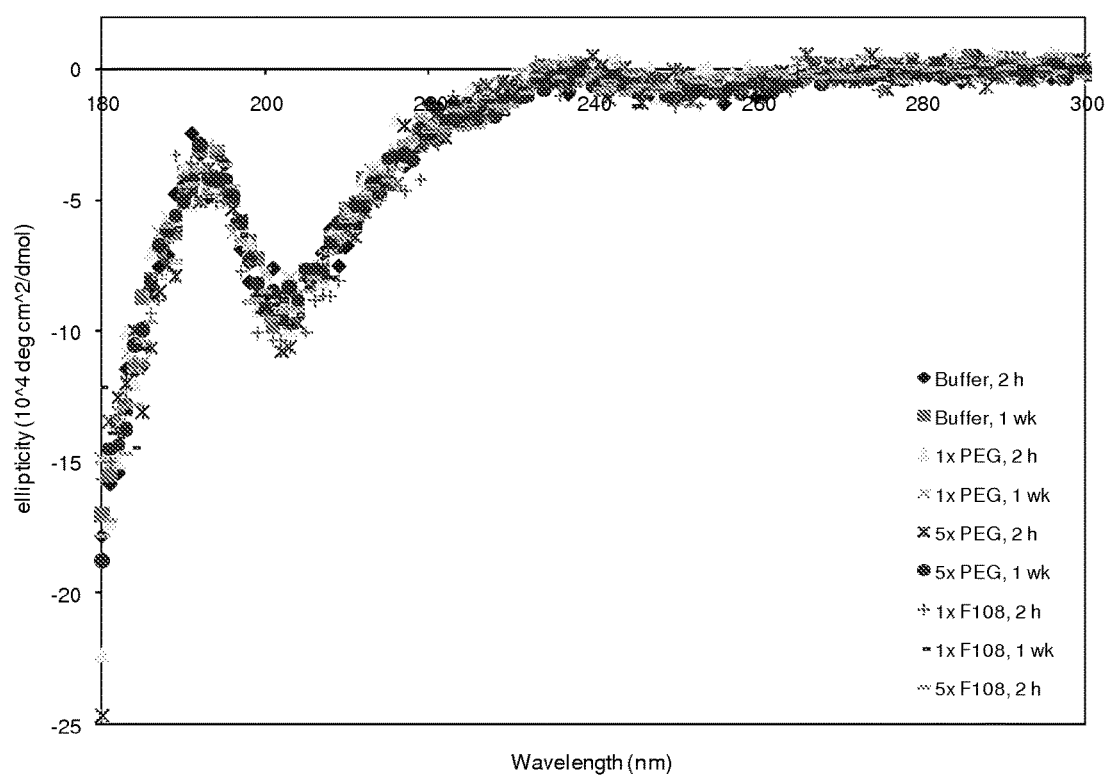
FIG. 18 shows the CD spectra of nisin incubated in nanoparticle-free solutions for 2 h and 1 week. Nisin concentration was 0.5 mg/mL. "1×" refers to a PEG concentration of 0.85 mg/mL or a F108 concentration of 2.08 mg/mL; "5×" refers to a PEG concentration of 4.25 mg/mL or a F108 concentration of 10.4 mg/mL.

FIG. 18 shows CD spectra of nisin incubated in (nanoparticle-free) solutions containing F108 or polyethylene glycol (PEG) at selected concentrations, for 2 h and 1 week. The molecular weight of PEG (MW 6000) was selected to approximate that of a single PEO chain in the F108 triblock (MW about 5700). As shown in FIG. 6, the spectra for nisin in all groups are quite similar, implying that neither F108 nor PEG had any effect on nisin conformation. In addition, these spectra provide no evidence of structure change upon nisin incubation in solution, whether for 2 h or 1 week.

Figure 19A:
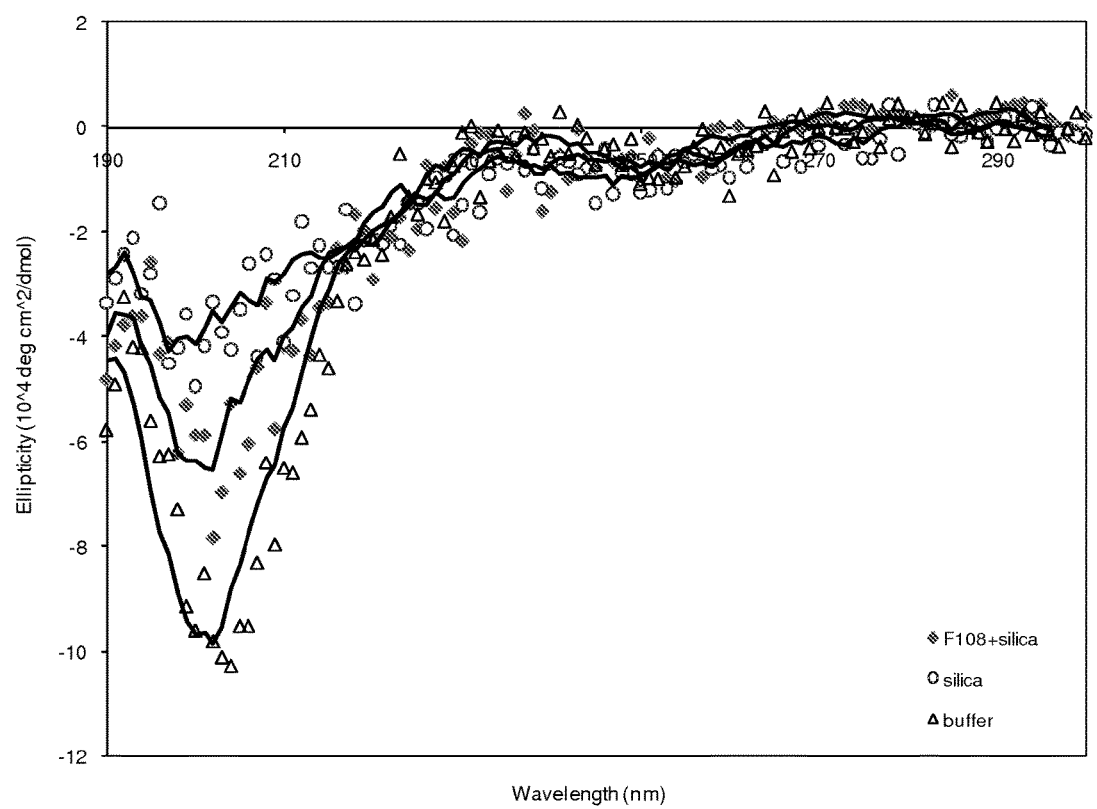
FIGS. 19A and 19B show the CD spectra of nisin contacted with F108-coated and uncoated hydrophobic silica nanoparticles and incubated in 10 mM sodium phosphate buffer (pH 7) at 25° C., for (a) 4 h (FIG. 19A); and (b) 1 week (FIG. 19B). Nisin concentration was 0.5 mg/mL.
Figure 19B:
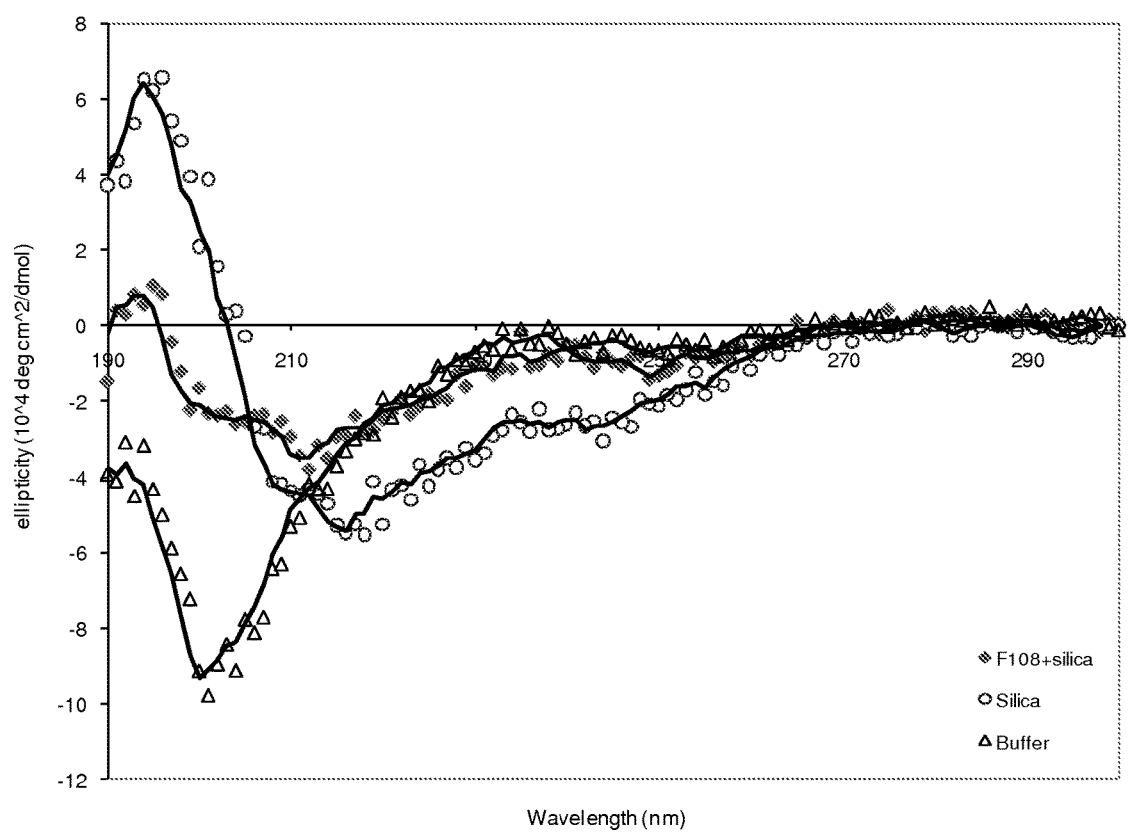

FIG. 19 shows CD spectra of nisin suspended with hydrophobic silica particles in sodium phosphate buffer (pH 7) at 25° C., after incubation for 4 h (FIG. 19a) and 1 week (FIG. 19b). An upward shift in ellipticity between 190 and 215 nm is evident upon contact with the nanoparticles after 4 h. However, in comparison to the uncoated particle sample, nisin spectra recorded in suspension with F108-coated nanoparticles remained more similar to spectra recorded for nisin in the absence of particles. A more substantial upward shift in ellipticity between 190 and 215 nm is evident after contact with the nanoparticles for 1 week. Again, however, nisin spectra recorded in suspension with F108-coated nanoparticles were considerably less altered than those recorded for nisin in suspension with uncoated nanoparticles. FIG. 19b also shows that nisin spectra remained substantially similar for F108-coated nanoparticle suspensions and particle-free solutions beyond 220 nm, while spectra recorded for uncoated nanoparticles differed from the other two samples in this region. These results suggest that nisin experienced greater structural alteration in suspension with uncoated, hydrophobic silica than in suspension with F108-coated surfaces.

Figure 20A:
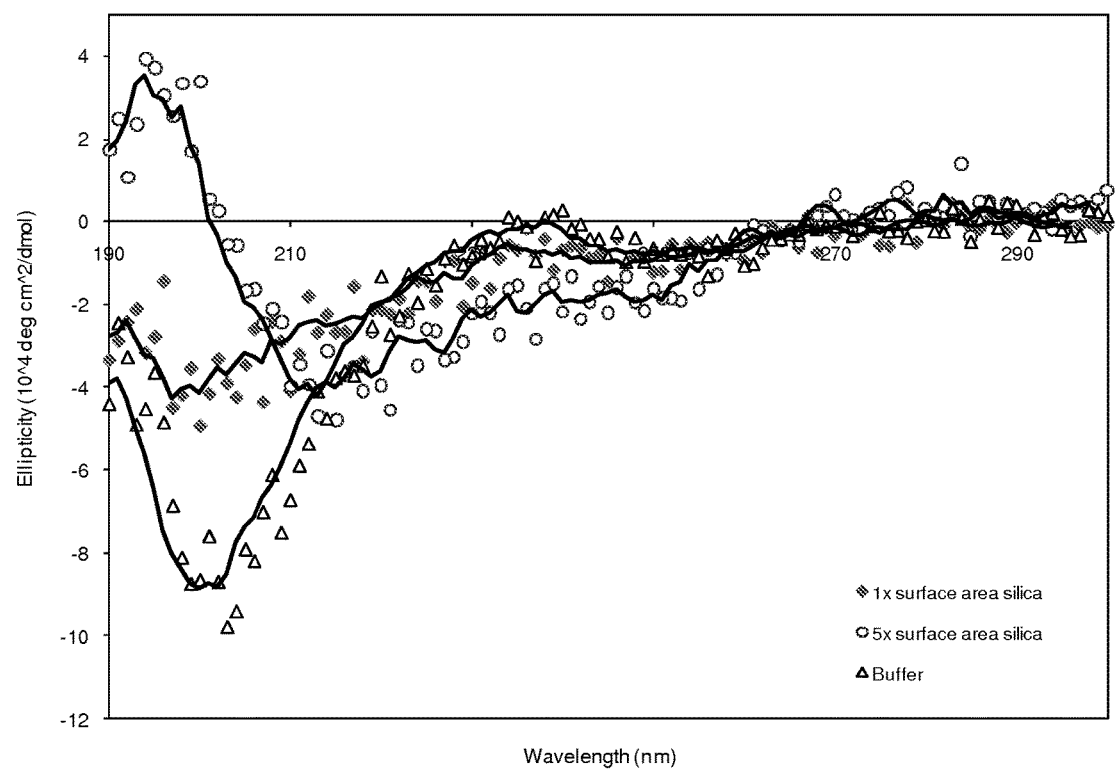
FIGS. 20A and 20B show the CD spectra of nisin contacted with (a) uncoated hydrophobic silica nanoparticles (FIG. 20A); and (b) F108-coated silica nanoparticles (FIG. 20B). Incubation time was 4 h in each case. Nisin concentration was 0.5 mg/mL. "1×" refers to a nanoparticle concentration of 2.19 mg/mL and F108 concentration (FIG. 20B) of 1.35 mg/mL; "5×" refers to a nanoparticle concentration of 11.0 mg/mL and F108 concentration (FIG. 20B) of 6.75 mg/mL.
Figure 20B:
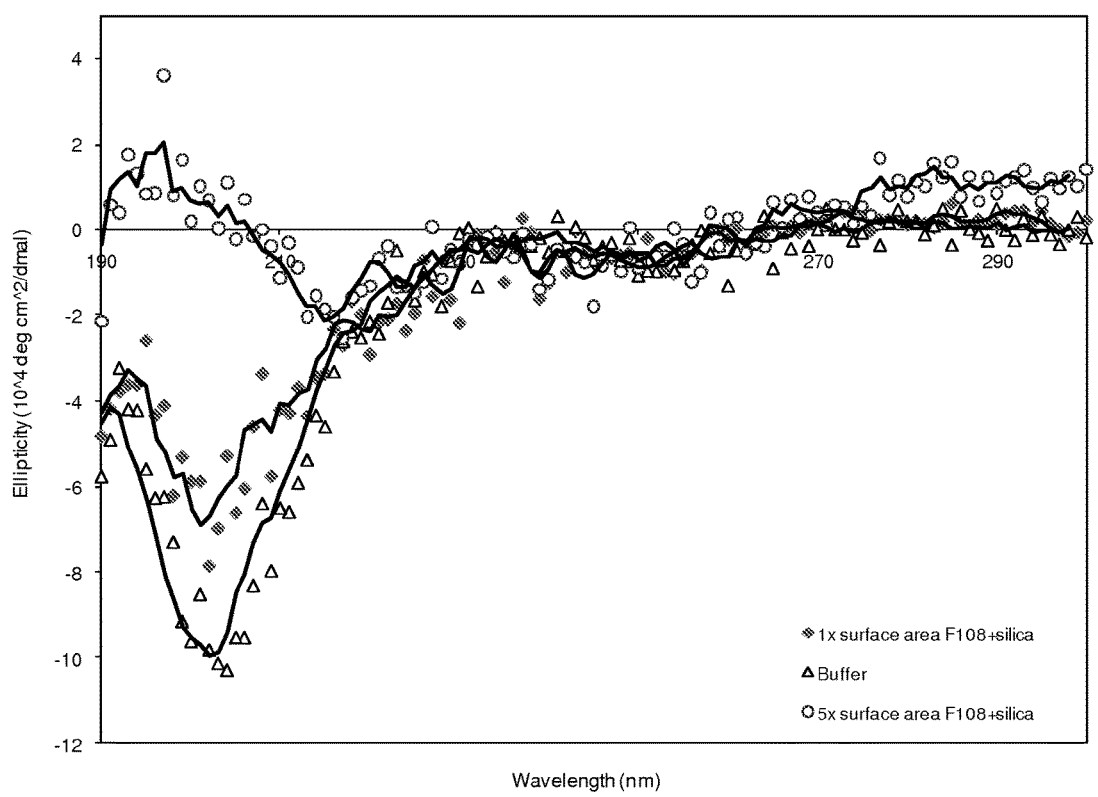

FIG. 20 shows the effects of increasing surface area on CD spectra of nisin suspended with uncoated (FIG. 20a) and F108-coated silica nanoparticles (FIG. 20b) after incubation for 4 h. An increase in particle surface area would provide more opportunity for nisin structural alteration if, at the particle concentrations used above, some nisin had remained unbound or otherwise not closely associated with the interface (e.g., residing in a diffuse outer layer). FIG. 20 shows that an upward shift in ellipticity between 190 and 215 nm is evident upon contact with a 5-fold increase in particle surface area in each case. FIG. 20 also shows that, upon a 5-fold increase in uncoated particle surface area, nisin spectra beyond 215 nm continued to deviate from that recorded at lower surface area, while nisin suspensions with high and low amounts of F108-coated particles showed substantially similar spectra beyond 215 nm. Analogous to the effects of incubation time presented in FIG. 19, these results show that relative to nisin spectra recorded in (particle-free) solution, nisin spectra recorded in suspension with F108-coated nanoparticles remained considerably less altered than those recorded for nisin in suspension with uncoated nanoparticles. These results suggest that nisin experienced greater structural alteration when adsorbed to bare, hydrophobic particles than when adsorbed to the same particles previously coated with F108.

REFERENCES

[1] J. N. Hansen, Nisin as a model food preservative. Crit Rev Food Sci Nutr 34 (1994) 69-93.

[2] J. Andersson, R. Larsson, R. Richter, K. N. Ekdahl, and B. Nilsson, Binding of a model regulator of complement activation (RCA) to a biomaterial surface: surface-bound factor H inhibits complement activation. Biomaterials 22 (2001) 2435-43.

[3] J. H. Lee, J. Kopecek, and J. D. Andrade, Protein-resistant surfaces prepared by PEO-containing block copolymer surfactants. J Biomed Mater Res 23 (1989) 351-68.

[4] J. T. Li, J. Carlsson, S.-C. Huang, and K. D. Caldwell, Adsorption of poly(ethylene oxide)-containing block copolymers: a route to protein resistance. in: J. E. Glass, (Ed.), Hydrophillic Polymers. Performance with environmental acceptability, American Chemical Society, Washington, D.C., 1996, pp. 61-78.

[5] J. T. Li, and K. D. Caldwell, Plasma protein interactions with PLURONIC™-treated colloids. Colloids and Surfaces B: Biointerfaces 7 (1996) 9-22.

[6] T. McPherson, K. Park, and S. Jo, Grafting of biocompatible hydrophilic polymers onto inorganic and metal surfaces, USPTO, United States Surgical (Norwalk, Conn.), USA, 2000.

[7] C. Maechling-Strasser, P. Dejardin, J. C. Galin, A. Schmitt, V. Housse-Ferrari, B. Sebille, J. N. Mulvihill, and J. P. Cazenave, Synthesis and adsorption of a poly(N-acetylethyleneimine)-polyethyleneoxide-poly(N-acetylethyleneimine) triblock-copolymer at a silica/solution interface. Influence of its preadsorption on platelet adhesion and fibrinogen adsorption. J Biomed Mater Res 23 (1989) 1395-410.

[8] N. D. Winblade, I. D. Nikolic, A. S. Hoffman, and J. A. Hubbell, Blocking adhesion to cell and tissue surfaces by the chemisorption of a poly-L-lysine-graft-(poly(ethylene glycol); phenylboronic acid) copolymer. Biomacromolecules 1 (2000) 523-33.

[9] D. K. Han, K. B. Lee, K. D. Park, C. S. Kim, S. Y. Jeong, Y. H. Kim, H. M. Kim, and B. G. Min, In vivo canine studies of a Sinkhole valve and vascular graft coated with biocompatible PU-PEO-503. Asaio J 39 (1993) M537-41.

[10] N. D. Winblade, H. Schmokel, M. Baumann, A. S. Hoffman, and J. A. Hubbell, Sterically blocking adhesion of cells to biological surfaces with a surface-active copolymer containing poly(ethylene glycol) and phenylboronic acid. J Biomed Mater Res 59 (2002) 618-31.

[11] K. Webb, K. Caldwell, and P. A. Tresco, Fibronectin immobilized by a novel surface treatment regulates fibroblast attachment and spreading. Crit Rev Biomed Eng 28 (2000) 203-8.

[12] J. A. Neff, K. D. Caldwell, and P. A. Tresco, A novel method for surface modification to promote cell attachment to hydrophobic substrates. J Biomed Mater Res 40 (1998) 511-9.

[13] J. A. Neff, P. A. Tresco, and K. D. Caldwell, Surface modification for controlled studies of cell-ligand interactions. Biomaterials 20 (1999) 2377-93.

[14] T. Basinska, and K. D. Caldwell, Colloid particles as immunodiagnostics: preparation and FFF characterization, In Chromatography of Polymers: Hyphenated and Multidimensional Techniques., American Chemical Society, Washington D.C., 1999, pp. 163-177.

[15] J. T. Li, J. Carlsson, J. N. Lin, and K. D. Caldwell, Chemical modification of surface active poly(ethylene oxide)-poly (propylene oxide) triblock copolymers. Bioconjug Chem 7 (1996) 592-9.

[16] G. L. Ellman, Tissue sulfhydryl groups. Arch Biochem Biophys 82 (1959) 70-7.

[17] I. Wiedemann, E. Breukink, C. van Kraaij, O. P. Kuipers, G. Bierbaum, B. de Kruijff, and H. G. Sahl, Specific binding of nisin to the peptidoglycan precursor lipid II combines pore formation and inhibition of cell wall biosynthesis for potent antibiotic activity. J Biol Chem 276 (2001) 1772-9.

[18] H. E. van Heusden, B. de Kruijff, and E. Breukink, Lipid II induces a transmembrane orientation of the pore-forming peptide lantibiotic nisin. Biochemistry 41 (2002) 12171-8.

[19] V. Krisdhasima, J. McGuire, R. Sproull, J Colloid Interface Sci. 154 (1992) 337.

[20] Cuypers, P. A., Corsel, J. W., Janssen, M. P., Kop, J. M., Hermens, W. T., and Hemker, H. C. (1983). The adsorption of prothrombin to phosphatidylserine multilayers quantitated by ellipsometry. J Biol Chem 258, 2426-2431.

[21] Calonder, C., Tie, Y., and Van Tassel, P. R. (2001). History dependence of protein adsorption kinetics. Proc Natl Acad Sci USA 98, 10664-10669.

[22] Tie, Y., Calonder, C., and Van Tassel, P. R. (2003). Protein adsorption: kinetics and history dependence. J Colloid Interface Sci 268, 1-11.

The invention claimed is:

1. A method of coating a substrate using an antimicrobial construct to prevent or inhibit microbial growth on the substrate, the method comprising:
providing an antimicrobial construct, the antimicrobial construct comprising an antimicrobial block copolymer which has an antimicrobial peptide component coupled to a block copolymer component;
applying the antimicrobial construct to the substrate, wherein a first portion of the block copolymer component adsorbs to the surface of the substrate and a second portion of the block copolymer component forms a flexible tether from the first portion of the block copolymer component to a quantity of the antimicrobial peptide component, and wherein applying the antimicrobial construct to the substrate imparts greater antimicrobial activity to the substrate than applying an antimicrobial peptide alone.

2. The method according to claim 1 wherein the antimicrobial construct is applied for sufficient time to permit the antimicrobial construct to form a barrier on the substrate to prevent or inhibit microbial growth on the substrate.

3. The method according to claim 1 wherein the antimicrobial construct is applied for sufficient time to permit a portion of the block copolymer to adhere to the substrate and form an antimicrobial coating on the substrate.

4. The method according to claim 1 wherein the substrate comprises tissue.

5. The method according to claim 1 wherein the substrate comprises a medical device, medical equipment, or an item in an antiseptic or sterile environment.

6. The method according to claim 1 wherein the substrate comprises a device which is applied to a patient's body or inserted into a patient's body.

7. The method according to claim 1 wherein the substrate comprises a device which contacts body fluids.

8. The method according to claim 1 wherein the substrate comprises an encapsulation device for cells, drugs or biologics.

9. The method according to claim 1 wherein the substrate comprises a drug delivery device.

10. The method according to claim 1 wherein the substrate comprises a personal care product.

11. The method according to claim 1 wherein the substrate comprises an industrial product.

12. The method according to claim 1 wherein the antimicrobial construct is provided in a preparation for applying to the substrate for preventing or inhibiting microbial growth on the substrate.

13. The method according to claim 12 wherein the preparation comprises a wound treatment.

14. The method according to claim 13 wherein the wound treatment comprises a biocompatible antimicrobial construct having a high water content.

15. The method according to claim 13 wherein the wound treatment comprises a topical antimicrobial product for application to the skin, a wound, a surgical site or the surface of a substrate.

16. The method according to claim 12 wherein the preparation comprises a cleaning solution.

17. The method according to claim 16 wherein the preparation comprises a cleaning solution for direct application to tissue.

18. The method according to claim 16 wherein the preparation comprises a cleaning solution for a medical device.

19. The method according to claim 16 wherein the cleaning solution comprises an oral care product.

20. A method of using an antimicrobial construct to prevent or inhibit biofilm formation on a substrate comprising:
- providing an antimicrobial construct, the antimicrobial construct comprising an antimicrobial block copolymer which has an antimicrobial peptide component coupled to a block copolymer component; and
- applying the antimicrobial construct to the substrate, wherein a portion of the block copolymer component forms a flexible tether from the block copolymer component to a quantity of the antimicrobial peptide, and a portion of the block copolymer component adsorbs to the surface of the substrate to prevent or inhibit biofilm formation, and wherein applying the antimicrobial construct to the substrate imparts greater antimicrobial activity to the substrate than applying an antimicrobial peptide alone, and wherein applying the antimicrobial construct to the substrate prevents or inhibits biofilm formation on the substrate.

21. The method of using the antimicrobial construct according to claim 20 wherein the substrate is tissue.

22. The method of using the antimicrobial construct according to claim 20 wherein the antimicrobial construct is applied to a patient having a wound to prevent or inhibit biofilm formation in the wound.

23. A composition for use in the treatment or prevention of microbial growth on a substrate comprising:
- a dispersion, gel, foam, emulsion or powder comprising particles of an antimicrobial construct, which is applied to a substrate, the antimicrobial construct comprising a block copolymer coupled to an antimicrobial peptide component, wherein a first portion of the block copolymer is capable of adsorbing or bonding to the substrate, and a second portion of the of the block copolymer forms a flexible tether from the first portion of the block copolymer to a quantity of the antimicrobial peptide component, and wherein the antimicrobial construct impart greater antimicrobial activity to the substrate than applying an antimicrobial peptide alone.

24. The composition according to claim 23 wherein the block copolymer comprises a functional group to form an end-group activated copolymer.

25. The composition according to claim 24 wherein the functional group comprises a reactive group suitable for reaction with the antimicrobial peptide.

26. The composition according to claim 24 wherein the functional group comprises a reactive group which is stable in an aqueous environment.

27. A substrate coated with an antimicrobial coating comprising:
- a substrate; and
- an antimicrobial coating, a portion of which is adhered or bonded to the substrate to coat the substrate and impart antimicrobial activity directly to the substrate, the antimicrobial coating comprising an antimicrobial block copolymer construct which has an antimicrobial peptide component, wherein a quantity of the antimicrobial component is attached to the block copolymer in a manner to form a flexible tether and a quantity of the block copolymer component adsorbs to the surface of the substrate, and wherein the block copolymer construct provides antimicrobial activity through the tethered antimicrobial peptide component, and wherein the antimicrobial coating on the substrate imparts greater antimicrobial activity to the substrate than applying an antimicrobial peptide alone.

28. The substrate according to claim 27 wherein the substrate comprises a tissue scaffold and the block copolymer forms a coating on the tissue scaffold.

29. A coated substrate coated with an antimicrobial composition for use in the treatment or prevention of microbial growth on a substrate, the coated substrate comprising:
- a substrate; and
- an antimicrobial composition adhered or bonded to the substrate, the antimicrobial composition comprising:
  (i) a first antimicrobial agent comprising a lantibiotic; and
  (ii) a block copolymer covalently coupled to the first antimicrobial agent, the block copolymer comprising a first hydrophobic copolymer portion which adheres or bonds to the substrate, and a second copolymer portion which forms a flexible tether from the first copolymer portion to the coupled first antimicrobial agent, wherein the substrate having the antimicrobial coating adhered or bonded to the substrate has greater antimicrobial activity than a substrate coated with the lantibiotic alone.

30. The coated substrate according to claim 29 further comprising a second antimicrobial agent, wherein a portion of the second antimicrobial agent is entrapped in the block co-polymer, and wherein the second antimicrobial agent is the same or different than the first antimicrobial agent.

* * * * *